United States Patent
Seykora

(10) Patent No.: US 9,555,034 B2
(45) Date of Patent: *Jan. 31, 2017

(54) COMPOSITIONS AND METHODS FOR TREATING SKIN CANCER ASSOCIATED DISEASES

(71) Applicant: The Trustees of the University of Pennsylvania, Philadelphia, PA (US)

(72) Inventor: John T. Seykora, Broomall, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/803,352

(22) Filed: Jul. 20, 2015

(65) Prior Publication Data

US 2015/0335644 A1 Nov. 26, 2015

Related U.S. Application Data

(63) Continuation of application No. 13/786,926, filed on Mar. 6, 2013, now Pat. No. 9,084,790, which is a continuation-in-part of application No. PCT/US2012/021732, filed on Jan. 18, 2012.

(60) Provisional application No. 61/434,078, filed on Jan. 19, 2011.

(51) Int. Cl.
| | |
|---|---|
| A61K 31/04 | (2006.01) |
| A01N 33/18 | (2006.01) |
| A01N 31/04 | (2006.01) |
| A61K 31/519 | (2006.01) |
| A61K 31/4709 | (2006.01) |
| A61K 31/4745 | (2006.01) |
| A61K 31/506 | (2006.01) |
| A61K 31/277 | (2006.01) |
| A61K 31/4184 | (2006.01) |
| A61K 31/517 | (2006.01) |
| A61K 45/06 | (2006.01) |
| A61K 9/00 | (2006.01) |
| A61K 47/10 | (2006.01) |
| A61K 47/20 | (2006.01) |
| A61K 31/33 | (2006.01) |

(52) U.S. Cl.
CPC .......... *A61K 31/519* (2013.01); *A61K 9/0014* (2013.01); *A61K 31/277* (2013.01); *A61K 31/4184* (2013.01); *A61K 31/4709* (2013.01); *A61K 31/4745* (2013.01); *A61K 31/506* (2013.01); *A61K 31/517* (2013.01); *A61K 45/06* (2013.01); *A61K 47/10* (2013.01); *A61K 47/20* (2013.01); *A61K 31/33* (2013.01)

(58) Field of Classification Search
None
See application file for complete search history.

(56) References Cited

U.S. PATENT DOCUMENTS

| | | | | |
|---|---|---|---|---|
| 2010/0074909 A1* | 3/2010 | Chang | ................. | A61K 31/444 424/174.1 |
| 2011/0224223 A1* | 9/2011 | Shokat | ................. | C12Q 1/485 514/252.18 |

OTHER PUBLICATIONS

Eustace, Alexander J. Investigation of response and resistance to dasatinib in melanoma cell lines. Diss. Dublin City University, 2010.*
Nguyen et al. J. Am. Acad. Dermatol. (2009), vol. 61, pp. 921-942.*
Kupferman et al. Journal of Experimental Therapeutics and Oncology (2009), vol. 8.2, pp. 117-127.*
Midena et al. B. J. Ophthalmol (2000), vol. 84, pp. 268-272.*

* cited by examiner

*Primary Examiner* — Patrick Lewis
(74) *Attorney, Agent, or Firm* — Mark S. Cohen; Pearl Cohen Zedek Latzer Baratz LLP

(57) ABSTRACT

The invention provides compositions and methods for treating skin cancer associated diseases. Specifically, the invention relates to topically administering a signaling pathway inhibitor or a related compound to treat pre-cancerous skin lesions, skin tumors, and their associated diseases or disorders.

46 Claims, 15 Drawing Sheets

COMPOSITIONS AND METHODS FOR TREATING SKIN CANCER ASSOCIATED DISEASES

CROSS REFERENCE TO RELATED APPLICATIONS

This application is a Continuation application of U.S. patent application Ser. No. 13/786,926, filed Mar. 6, 2013, which claims priority to International Patent Application PCT/US12/21732, filed Jan. 18, 2012, which claims priority to U.S. Provisional Patent Application 61/434,078, filed Jan. 19, 2011, each of which is incorporated by reference herein in its entirety.

FIELD OF THE INVENTION

The invention relates to compositions and methods for treating skin cancer associated diseases. Specifically, the invention relates to topically administering tyrosine kinase inhibitors and related compounds to treat pre-cancerous skin lesions, skin tumors, and their associated diseases or disorders.

BACKGROUND OF THE INVENTION

Actinic keratosis (AK) is the most common precancerous lesion - manifesting as thickened scaly or crusty patches of skin - in humans, and its treatment represents a common reason for patients to see a dermatologist. Recent studies estimate that there are approximately 58 million AKs in the US population leading to 5.2 million office visits per year with an approximate cost of 0.9-1.2 billion dollars. The risk for developing an AK is directly related to the degree of photodamage which is a function of age, sun exposure, and Fitzpatrick-skin type (being more common in fair-skinned people). Studies show that multiple AKs significantly decrease the quality of life in patients, leading some investigators to use the term 'actinic neoplasia syndrome' for such patients. Some of these pre-cancers progress to squamous cell carcinoma (cSCC), which is discussed below.

Current AK treatments involve topical and destructive modalities. AKs can be treated by freezing the skin with liquid nitrogen ($N_2$). Although technically simple, this therapy has adverse effects which include dyspigmentation, pain, stinging, and a low efficacy rate; liquid $N_2$ is associated with only an 83% clearance rate and lacks specificity for lesional cells requiring the freezing of at least 1 mm of surrounding non-lesional tissue. Other commonly used destructive therapies include: curettage and surgical excision. Since patients often have many AKs requiring treatment; this limits the use of destructive modalities because of the cosmetic deficits associated with dyspigmentation and scarring.

The primary topical agents to treat AKs are 5-fluorouracil (5-FU), imiquimod (ALDARA®), and diclofenac (e.g., SOLARAZE®) 5-FU is a chemotherapeutic agent that inhibits RNA and DNA synthesis and targets dividing cells which are more prevalent in AKs than adjacent epidermis. 5-FU is used as 0.5%, 2.5%, or 5.0% formulations which correspond to compound concentrations of (36-360 mM). 5-FU has significant side effects including prominent inflammation, ulceration, and even scarring; given these side-effects, topical 5-FU is associated with a lower quality of life for patients. Imiquimod, a Toll receptor 7 agonist, produces prominent inflammation to eliminate AKs. The prominent inflammation stimulated by imiquimod is irritating and mimics psoriasis, and this reaction has been associated with autoimmune reactions such as alopecia areata and vitiligo. Another common topical agent to treat AKs is diclofenac, a topical non-steroidal anti-inflammatory compound with an unclear mechanism of action on actinic keratoses. Recent studies using diclofenac and imiquimod showed therapeutic weaknesses associated with poor clearance rates and significant irritation.

Overall, the most commonly used topical agents to treat AKs have significant negative features including irritation, decreased quality of life, and limited efficacy. cSCC is the second most common form of cancer with an annual incidence of 620,000 cases annually. According to some studies, cSCCs cause approximately 8,000 cases of nodal metastasis leading to 3,000 deaths in the US alone each year. In 2004, the estimated cost of treating cSCCs in the US alone was approximately 500 million dollars. The risk factors for cSCCs are similar to those for AKs and include age, male sex, and cumulative UV exposure from sunlight or tanning salons. Since Americans are living longer, spending more time outdoors, and not adequately using sunscreens, it is likely that the numbers of cSCCs in the United States will increase, as will the cost to treat them.

Accordingly, there exists a need for improved therapy modalities and compositions to treat pre-cancerous skin lesions, skin tumors, and their associated diseases or disorders.

SUMMARY OF THE INVENTION

In one aspect, methods are provided for treating a pre-cancerous skin lesion in a subject, the methods include: topically administering to said subject a therapeutically effective amount of a tyrosine kinase inhibitor (e.g., an Src family kinase inhibitor) or related compound, thereby treating said skin lesion in said subject.

In another aspect, methods are provided for treating a skin tumor in a subject, the methods include: topically administering to said subject a therapeutically effective amount of a tyrosine kinase inhibitor (e.g., an Src family kinase inhibitor) or related compound, thereby treating said skin tumor in said subject.

In a further aspect, methods are provided for treating an actinic keratosis in a subject, the methods include: topically administering to said subject a therapeutically effective amount of a tyrosine kinase inhibitor (e.g., an Src family kinase inhibitor) or related compound, thereby treating said actinic keratosis in said subject.

In yet another aspect, methods are provided for treating a cutaneous squamous cell carcinoma in a subject, the methods include: topically administering to said subject a therapeutically effective amount of a tyrosine kinase inhibitor (e.g., an Src family kinase inhibitor) or related compound.

In yet another aspect, compositions are provided, the compositions include: a topical formulation of a tyrosine kinase inhibitor or related compound present in an amount effective to topically treat a skin cancer related disease or disorder (e.g., a pre-cancerous skin lesion, a skin tumor, an actinic keratosis, a squamous cell carcinoma in situ like lesion and/or a cutaneous squamous cell carcinoma).

In yet another aspect, methods are provided for treating a skin cancer related disease or disorder (e.g., a pre-cancerous skin lesion, a skin tumor, an actinic keratosis, a squamous cell carcinoma in situ like lesion and/or a cutaneous squamous cell carcinoma) in a subject, the methods include:

topically administering to said subject a therapeutically effective amount of a PI3K/PDK1/AKT signaling pathway inhibitor.

In yet another aspect, compositions are provided, the compositions include: a topical formulation of a PI3K/PDK1/AKT signaling pathway inhibitor present in an amount effective to topically treat a skin cancer related disease or disorder (e.g., a pre-cancerous skin lesion, a skin tumor, an actinic keratosis, a squamous cell carcinoma in situ like lesion and/or a cutaneous squamous cell carcinoma).

In yet another aspect, methods are provided for treating a skin cancer related disease or disorder (e.g., a pre-cancerous skin lesion, a skin tumor, an actinic keratosis, a squamous cell carcinoma in situ like lesion and/or a cutaneous squamous cell carcinoma) in a subject, the methods include: topically administering to said subject a therapeutically effective amount of a MAPK/ERK signaling pathway inhibitor.

In yet another aspect, compositions are provided, the compositions include: a topical formulation of a MAPK/ERK signaling pathway inhibitor present in an amount effective to topically treat a skin cancer related disease or disorder (e.g., a pre-cancerous skin lesion, a skin tumor, an actinic keratosis, a squamous cell carcinoma in situ like lesion and/or a cutaneous squamous cell carcinoma).

In yet another aspect, methods are provided for treating a skin cancer related disease or disorder (e.g., a pre-cancerous skin lesion, a skin tumor, an actinic keratosis, a squamous cell carcinoma in situ like lesion and/or a cutaneous squamous cell carcinoma) in a subject, the methods include: topically administering to said subject a therapeutically effective amount of a JAK-STAT signaling pathway inhibitor.

In yet a further aspect, compositions are provided, the compositions include: a topical formulation of a JAK-STAT signaling pathway inhibitor present in an amount effective to topically treat a skin cancer related disease or disorder (e.g., a pre-cancerous skin lesion, a skin tumor, an actinic keratosis, a squamous cell carcinoma in situ like lesion and/or a cutaneous squamous cell carcinoma).

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description. It is also contemplated that whenever appropriate, any embodiment of the present invention can be combined with one or more other embodiments of the present invention, even though the embodiments are described under different aspects of the present invention.

The area of each tumor was followed over time and the relative area remaining for each tumor was calculated by comparing the area at each time point to the area at time 0. The average relative tumor area value was calculated for each cohort at the indicated times with the standard error. p values were calculated using a T-test for means.

Figure 13:
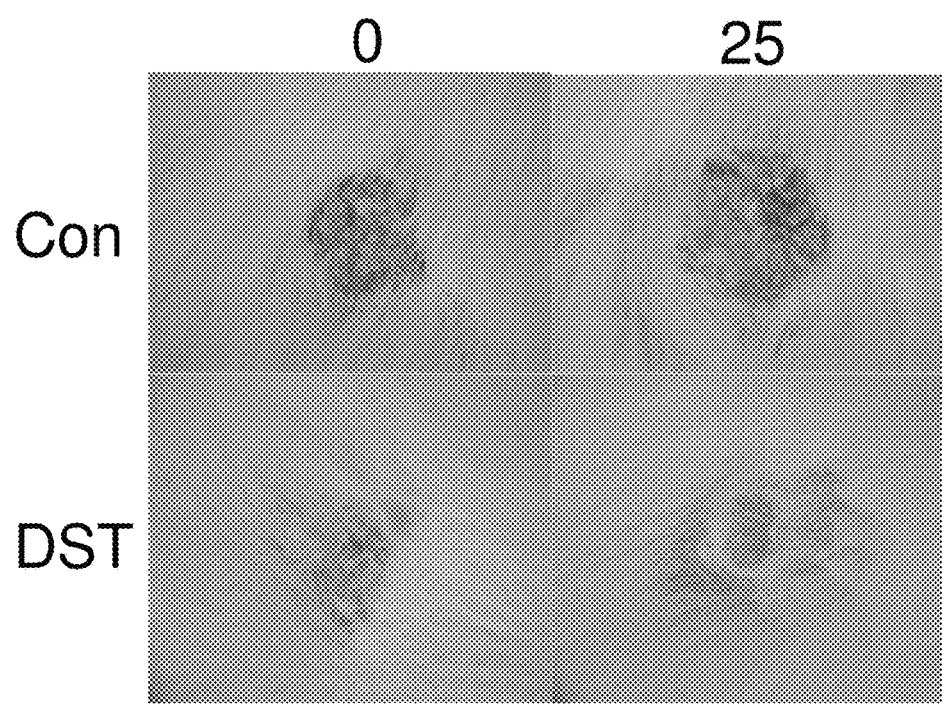

FIG. 13 shows that topical dasatinib induces clearance of cSCCs in K14-Fyn Y528F mice. 1% dasatinib (DST) ointment was topically applied daily (Monday-Friday) for 25 applications-numbers indicate treatments. Clearance of a back cSCC was noted by 5 weeks. Application of vehicle (Con) did not clear a cSCC of similar size during the treatment period. Images were taken with dermatoscope under identical conditions.

Figure 14:
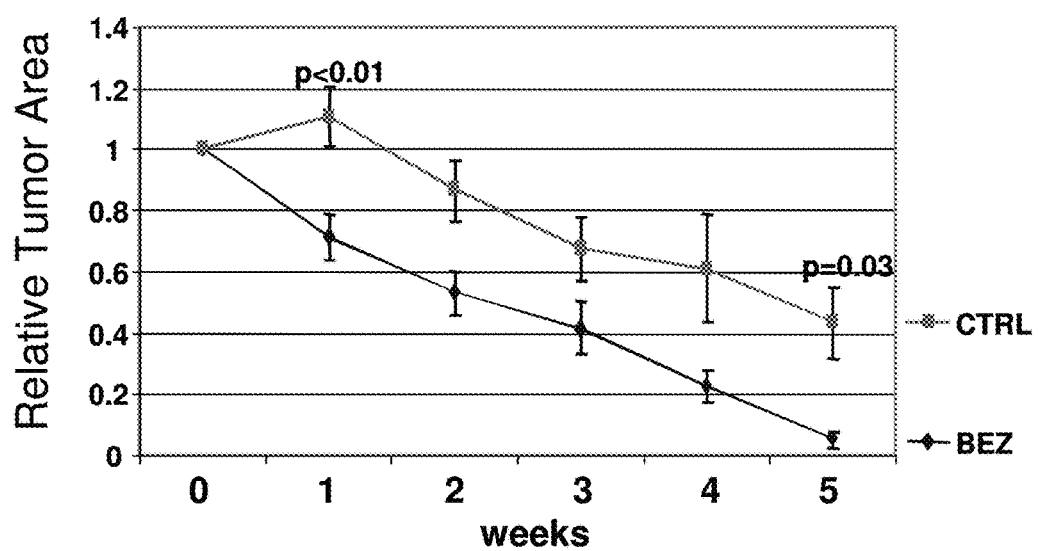

FIG. 14 shows that topical BEZ235 induces cSCC regression. Fifteen K14-Fyn Y528F mice with solitary cSCCs were given topical 20 mM BEZ235 ointment daily (Monday-Friday) for 25 applications. A control cohort of 15 mice was treated in parallel with ointment alone. The area of each tumor was followed over time and the relative area for each tumor was calculated by comparing the area at each time point to the area at time 0. The average relative tumor area value was calculated for each cohort at the indicated times with the standard error. p values were calculated using a T-test for means.

Figure 15:
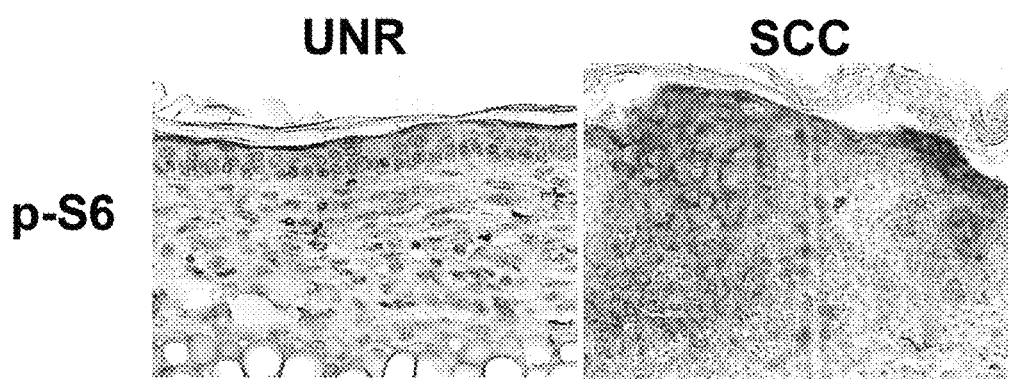

FIG. 15 shows that phosphorylation of S6 kinase, an mTOR substrate, is elevated in K14-Fyn Y528F mice in cSCCs (right panel) as compared to unremarkable tissue (left panel).

DETAILED DESCRIPTION OF THE INVENTION

The invention relates to compositions and methods for treating skin cancer associated diseases. Specifically, the invention relates to topically administering tyrosine kinase inhibitors or related compounds to treat pre-cancerous skin lesions, skin tumors, and their associated diseases or disorders, which include without limitation, actinic keratosis (AK), squamous cell carcinoma in situ like lesion (SCIS-like lesion) and cutaneous squamous cell carcinoma (cSCC).

In one embodiment, provided herein are methods for treating a pre-cancerous skin lesion in a subject, the methods comprising: topically administering to said subject a therapeutically effective amount of a tyrosine kinase inhibitor or related compound, thereby treating said skin lesion in said subject. In another embodiment, provided herein are methods for treating a skin tumor in a subject, the methods comprising: topically administering to said subject a therapeutically effective amount of a tyrosine kinase inhibitor or related compound, thereby treating said skin lesion in said subject.

In another embodiment, provided herein are methods for treating an actinic keratosis in a subject, the methods comprising: topically administering to said subject a therapeutically effective amount of a tyrosine kinase inhibitor or related compound, thereby treating said actinic keratosis in said subject. In another embodiment, provided herein are methods for treating cutaneous squamous cell carcinoma in a subject, the methods comprising: topically administering to said subject a therapeutically effective amount of a tyrosine kinase inhibitor or related compound, thereby treating said cutaneous squamous cell carcinoma in said subject.

The Applicants have surprisingly and unexpectedly found that administering tyrosine kinase inhibitors (e.g., an Src family kinase inhibitor) and related compounds treat pre-cancerous skin lesions, skin tumors, and their associated diseases or disorders. For example, topically administering PP2, dasatinib and BEZ235 surprisingly and unexpectedly induced the clearance of cutaneous squamous cell carcinoma and pre-cancerous lesions within a few weeks, as demonstrated herein.

The term "tyrosine kinase inhibitor" may refer to any of a variety of therapeutic agents or drugs that act as selective or non-selective inhibitors of receptor and/or non-receptor tyrosine kinases. Tyrosine kinase inhibitors and related compounds are well known in the art and described in U.S Patent Publication 2007/0254295, which is incorporated by reference herein in its entirety. It will be appreciated by one of skill in the art that a compound related to a tyrosine kinase inhibitor will recapitulate the effect of the tyrosine kinase inhibitor, e.g., the related compound will act on a different member of the tyrosine kinase signaling pathway to produce the same effect as would a tyrosine kinase inhibitor of that tyrosine kinase.

Examples of tyrosine kinase inhibitors and related compounds suitable for use in methods of embodiments of the present invention include, but are not limited to, dasatinib (BMS-354825), PP2, BEZ235, saracatinib, gefitinib (Iressa), sunitinib (Sutent; SU11248), erlotinib (Tarceva; OSI-1774), lapatinib (GW572016; GW2016), canertinib (CI 1033), semaxinib (SU5416), vatalanib (PTK787/ZK222584), sorafenib (BAY 43-9006), imatinib (Gleevec; STI571), leflunomide (SU101), vandetanib (Zactima; ZD6474), MK-2206 (84441-aminocyclobutyl)phenyl]-9-phenyl-1,2,4-triazolo[3,4-f] [1,6]naphthyridin-3(2H)-one hydrochloride) derivatives thereof, analogs thereof, and combinations thereof. Additional tyrosine kinase inhibitors and related compounds suitable for use in the present invention are described in, for example, U.S Patent Publication 2007/0254295, U.S. Pat. Nos. 5,618,829, 5,639,757, 5,728,868, 5,804,396, 6,100,254, 6,127,374, 6,245,759, 6,306,874, 6,313,138, 6,316,444, 6,329,380, 6,344,459, 6,420,382, 6,479,512, 6,498,165, 6,544,988, 6,562,818, 6,586,423, 6,586,424, 6,740,665, 6,794,393, 6,875,767, 6,927,293, and 6,958,340, all of which are incorporated by reference herein in their entirety.

In certain embodiments, the tyrosine kinase inhibitor is an Src family kinase (SFK) inhibitor.

In certain embodiments, the tyrosine kinase inhibitor or related compound has a molecular weight of less than 500 daltons.

In certain embodiments, the tyrosine kinase inhibitor is a small molecule kinase inhibitor that has been orally administered and that has been the subject of at least one Phase I clinical trial, more preferably at least one Phase II clinical, even more preferably at least one Phase III clinical trial, and most preferably approved by the FDA for at least one hematological or oncological indication. Examples of such inhibitors include, but are not limited to, Gefitinib, Erlotinib, Lapatinib, Canertinib, BMS-599626 (AC-480), Neratinib, KRN-633, CEP-11981, Imatinib, Nilotinib, Dasatinib, AZM-475271, CP-724714, TAK-165, Sunitinib, Vatalanib, CP-547632, Vandetanib, Bosutinib, Lestaurtinib, Tandutinib, Midostaurin, Enzastaurin, AEE-788, Pazopanib, Axitinib, Motasenib, OSI-930, Cediranib, KRN-951, Dovitinib, Seliciclib, SNS-032, PD-0332991, MKC-I (Ro-317453; R-440), Sorafenib, ABT-869, Brivanib (BMS-582664), SU-14813, Telatinib, SU-6668, (TSU-68), L-21649, MLN-8054, AEW-541, and PD-0325901.

Also provided herein are compositions comprising: a formulation for topical administration of a tyrosine kinase inhibitor (e.g., Src family kinase (SFK) inhibitor) or related compound amount effective to topically treat a skin cancer related disease or disorder. Src family kinases are well known in the art and described in U.S. Patent Publication 2008/0193504, which is incorporated by reference herein in its entirety. Members of the Src family include, for example, the following kinases in mammals: Src, Fyn, Yes, Fgr, Lyn, Hck, Lck, and Blk. These are nonreceptor protein kinases that range in molecular mass from about 52 Kd to about 62 Kd. All are characterized by a common structural organization having six distinct functional domains: Src homology domain 4 (SH4), a unique domain, SH3 domain, SH2 domain, a catalytic domain (SH1), and a C-terminal regulatory region. See Tatosyan et al. Biochemistry (Moscow) 65, 49-58 (2000).

As used herein, the terms "Src family tyrosine kinase inhibitor" "Src family kinase inhibitor" or "SFK inhibitor" may refer to any inhibitor of one or more kinases within the Src family of kinases.

SFK inhibitors are well known in the art and described in U.S. Patent Publication 2008/0193504, which is incorporated by reference herein in its entirety. In one embodiment, the SFK inhibitor PP2 (4-amino-5-(4-chlorophenyl)-7-(t-butyl)pyrazolo[3,4-d]-pyrimidine; also known as AG1879; Calbiochem MW0301.8) is used. PP2 is also described in J. H. Hanke et al., 1996, J. Biol. Chem, vol. 271, page 695; J.K.Chen et al., 2000, J. Biol. Chem, vol. 275, page 13789; and Yoshizumi et al., 2000, J. Biol. Chem., vol. 275, page 11706. In another embodiment the SFK inhibitor PP1 (Molecular Cell, 1999, 3: 639-648) is used. In another embodiment the SFK inhibitor SKI606 (Cancer Research, 2003, 63: 375) is used. In another embodiment, the SFK inhibitor AZD0530 (AstraZeneca, London UK) is used. In another embodiment, the SFK inhibitor SU6656 is used (Blake, R. A. et al. 2000. Mol. Cell. Biol. 20: 9018-9027). In another embodiment the SFK inhibitor dasatinib (BMS-354825)(N-(2-chloro-6-methylphenyl)-2-[[6-[4-(2-hydroxyethyl)-1-piperazinyl]-2-methyl-4-pyrimidinyl]amino]-5-thiazolecarboxamide, monohydrate) is used.

SFK inhibitors useful in the methods of the present invention also include, but are not limited to, SFK inhibitors described in International Patent Applications WO 96/10028; WO 97/07131; WO 97/08193; WO 97/16452; WO 97/28161; WO 97/32879; WO 97/49706; WO 01/94341; WO 02/16352; WO 02/30924; WO 02/30926; WO 02/34744; WO 02/085895; WO 02/092577; WO 02/092578; WO 02/092579; WO 03/008409 and WO 03/013540, all of which are incorporated by reference herein in their entirety.

Other examples of SFK inhibitors include, but are not limited to, 4-amino-5-(3-methoxyphenyl)-7-{4-[2-(2-methoxyethylamino)ethoxy]phenyl}pyrrolo[2,3 -d]pyrimidine and 4-amino-5-(3-methoxyphenyl) 7-(4-{2-[di-(2-methoxyethyl)amino]ethoxy}phenyl)pyrrolo [2,3-d] pyrimidine which are obtainable by methods described in International Patent Application WO 96/10028; 2-(2,6-dichloroanilino)-6,7-dimethyl-1,8-dihydroimidazo[4,5-h]isoquinolin-9-one and 2-(2,6-dichloroanilino)-7-[(E)-3-diethylaminoprop-1-enyl]-6-methyl 1,8-dihydroimidazo[4,5-h] isoquinolin-9-one which are obtainable by methods described in Journal Medicinal Chemistry, 2002, 45: 3394; 1-[6-(2,6-dichlorophenyl)-2-(4-diethylaminobutyl)pyrido[2,3-d]pyrimidin-7-yl]3-ethylurea which is obtainable by methods described in Journal Medicinal Chemistry, 1997, 40: 2296-2303 and Journal Medicinal Chemistry, 2001, 44, 1915; certain 4-anilino-3-cyanoquinoline derivatives (Journal Medicinal Chemistry, 2001, 44: 822-833 and 3965-3977); PD166285 (J. Pharmacol. Exp. Ther., 1997, 283: 1433-1444); PD162531 (Mol. Biol. Cell, 2000, 11: 51-64); PD166326 and PD180970 (Biochem. Pharmacol., 2000, 60: 885-898); PD173955 (Cancer Research, 1999, 59; 6145-6152); PD173952 (Blake, R. A. et al. 2000. Mol. Cell. Biol. 20: 9018-9027); Dasatinib or BMS354825 (Lombardo et al. 2004. J Med. Chem. 47:6658-6661); the pyrazolopyrimidine class of SFK inhibitors, such as 4-amino-5-(4-methylphenyl)-7-(t-butyl-) pyrazolo[3,4-d-]pyrimidine (AGL 1872), 4-amino-5-(4-chlorophenyl)-7-(t-butyl)pyrazolo[3 ,4-d-]pyrimidine (AGL 1879), and the like; the macrocyclic dienone class of SFK inhibitors, such as Radicicol R2146, Geldanamycin, Herbimycin A, and the like; the pyrido[2,3-d] pyrimidine class of SFK inhibitors; the 4-anilino-3-quinolinecarbonitrile class of SFK inhibitors; tyrphostin-derived inhibitors, which are derivatives of benzylidenemalonitrile (Ramdas et al., 1995, Archives of Biochemistry and Biophysics 323:237-242); derivatives of pyrazolopyrimidine PP1 (4-amino-5-(4-methylphenyl)-7-(t-butyl)pyrazolo[3,4-d]pyrimidine (Hanke et al., 1996, J. Biol. Chem. 271:695-791); angelmicin B and derivatives thereof (Yokoyama et al., 1996, Leukemia Research 20:491-497); compounds described in J Bone Mineral Research, 1999, 14: (Suppl. 1) 5487, Molecular Cell, 1999, 3: 639-647, Journal Medicinal Chemistry, 1997, 40: 2296-2303, Journal Medicinal Chemistry, 1998, 41: 3276-3292 and Bioorganic & Medicinal Chemistry Letters, 2002, 12: 1361 and 3153.

Additional SFK inhibitors useful in the methods the present invention are described in, for example, International Patent Applications WO 05/013983, WO 02/079192, WO 03/000188, WO 03/000266, WO 03/000705, WO 02/083668, WO 02/092573, WO 03/004492, WO 00/49018, WO 03/013541, WO 01/00207, WO 01/00213, WO 01/00214 and U.S. Patent Applications 2005/0096298, 2004/0266855, 2004/0204582, 2004/0167198, 2004/0014676, 2003/0207902, 2003/0119819 and 2002/0132819, all of which are incorporated by reference in their entirety.

In another embodiment, as described in U.S. Patent Publication 2008/0193504, small peptides which compete with larger phosphotyrosine peptides for binding to the Src kinase protein may be used to inhibit Src family kinases, in particular small phosphotyrosine containing peptide ligands, 5 to 6 amino acids, which are able to compete with larger phosphotyrosine-containing peptides and protein ligands for binding to SH2 domains, thereby inhibiting the Src family kinases. In another embodiment, small peptides which correspond to catalytic or enzymatic domains of Src kinase and would compete with Src kinase may be used to inhibit the activation of downstream components of the Src kinase signaling cascade. In another embodiment, SFK inhibitors include the use of larger polypeptides that inhibit Src kinase activity including, but not limited to, Csk (carboxyl-terminal Src kinase) which is a specific physiologic inhibitor of Src kinase. Further examples of larger polypeptides that inhibit Src kinase activity include, for example, Src dominant-negative mutants, i.e., Srck-(Barone et al., 1995, Nature 378:509-512) and Fyn dominant-negative mutants (Twamley-Stein et al., 1993, Proc. Natl. Acad. Sci. USA 90:7696-7700). In some embodiments, antibodies or other larger molecules that inhibit Src kinase activity may be used.

As used herein, the term, "selective" with respect to inhibition means preferential inhibition of a first activity relative to a second activity (e.g., preferential inhibition of one signaling pathway to another signaling pathway; preferential inhibition relative to other tyrosine kinase inhibitors; or preferential inhibition of a mutant to a wild-type or vice versa). In some embodiments, the inhibitor is greater than five times more selective, greater than ten times more selective, greater than fifty times more selective, greater than 100 times more selective, or greater than 1000 times more selective for the desired molecular target or pathway versus an undesired molecular target or pathway. In some embodiments, the inhibitor inhibits the first activity of the molecular target or pathway by at least 2-fold, at least 5-fold, at least 10-fold, at least 20-fold, at least 50-fold, at least 100-fold relative to the second activity of the molecular target or pathway under the same conditions. The activity of a molecular target or pathway may be measured by any reproducible means. The activity of a molecular target or pathway may be measured in vitro or in vivo.

As used herein, "modulating" refers to "stimulating" or "inhibiting" an activity of a molecular target or pathway. In one aspect, a composition modulates the activity of a molecular target or pathway if it stimulates or inhibits the activity of the molecular target or pathway by at least 10%, by at least about 10%, by at least about 20%, by at least about 25%, by at least about 30%, by at least about 40%, by at least about 50%, by at least about 60%, by at least about 70%, by at least about 75%, by at least about 80%, by at least about 90%, by at least about 95%, by at least about 98%, or by about 99% or more relative to the activity of the molecular target or pathway under the same conditions but lacking only the presence of the composition. In one aspect, the composition modulates the activity of a molecular target or pathway if it stimulates or inhibits the activity of the molecular target or pathway by at least 2-fold, at least 5-fold, at least 10-fold, at least 20-fold, at least 50-fold, at least 100-fold relative to the activity of the molecular target or pathway under the same conditions but lacking only the presence of the composition. The activity of a molecular target or pathway may be measured by any reproducible means. The activity of a molecular target or pathway may be measured in vitro or in vivo. For example, the activity of a molecular target or pathway may be measured in vitro or in vivo by an enzymatic activity assay. For example, samples or assays comprising one or more components of a protein kinase signaling pathway, such as one or more components of a PI3K/PDK1/AKT signaling pathway (e.g., mTOR), can be treated with the composition and compared to control samples without the composition. Control samples (untreated with the composition) can be assigned a relative activity value of 100%. A change in enzymatic activity caused by the composition can be measured in the assays. For example, the change in enzymatic activity can be characterized by the change in the extent of phosphorylation of certain substrates.

It will be appreciated that many of the inhibitors described herein are strong inhibitors of their targets. For example, an inhibitor has a binding inhibitory activity (IC$_{50}$ value) for its desired molecular target of 1000 µM or less, 1000 nM or less, 100 nM or less, 10 nM or less, or especially 1 nM or less. In another example, the inhibitor has a binding inhibitory activity (IC$_{50}$ value) for its desired molecular target of between 1000 µM and 1 nM, between 1000 µM and 10 nM, between 1000 µM and 100 nM, between 1000 µM and 1000 nM, between 1000 nM and 1 nM, between 1000 nM and 10 nM, between 1000 nM and 100 nM, between 100 nM and 10 nM, between 100 nM and 1 nM, or between 10 nM and 1 nM.

In some embodiments, the inhibitors disclosed herein inhibit their molecular targets or pathways by at least about 10%, by at least about 20%, by at least about 25%, by at least about 30%, by at least about 40%, by at least about 50%, by at least about 60%, by at least about 70%, by at least about 75%, by at least about 80%, by at least about 90%, by at least about 95%, by at least about 98%, or by about 99% or more.

As used herein, "phosphorylation" refers to the addition of phosphate groups to a substrate, including proteins and organic molecules; and, plays an important role in regulating the biological activities of proteins. In one aspect, the phosphorylation assayed and measured involves the addition of phosphate groups to tyrosine residues. The substrate can be a peptide or protein.

The Janus kinases (JAK) are a family of intracellular non-receptor tyrosine kinases that include JAKE JAK2, JAK3 and tyrosine kinase 2 (TYK2). The JAKs play a role in cytokine signaling. The downstream substrates of the JAK family of kinases include the signal tranducer activator of transcription (STAT) proteins. JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas. For a review of the pharmaceutical intervention of the JAK/STAT pathway see Frank, 1999, Mol. Med. 5:432:456 and Seidel et al., 2000, Oncogene 19:2645-2656.

Inhibitors of JAK/STAT include, but are not limited to, Ruxolitinib, Tofacitinib (tasocitinib; CP-690550), Baricitinib (LY3009104, INCB28050), CYT387, Lestaurtinib, Pacritinib (SB1518), TG101348.

The PI3K//PDK1/AKT/mTOR pathway is an intracellular signaling pathway important in apoptosis. Briefly, PI3K activation leads to activation of AKT which activates mammalian target of rapamycin (mTOR).

Inhibitors of PI3K include, but are not limited to, Wortmannin (an irreversible inhibitor of PI3K), demethoxyviridin (a derivative of wortmannin), LY294002 (a reversible inhibitor of PI3K), Perifosine, CAL101, PX-866, IPI-145, SF1126, INK1117, GDC-0941, BKM120, XL147 (also known as SAR245408), XL765 (also known as SAR245409), Palomid 529, GSK1059615, ZSTK474, PWT33597 (inhibits both PI3K and mTOR inhibitor), IC87114, TG100-115, CAL263, PI-103 (inhibits both PI3K and mTOR inhibitor), GNE-477 (inhibits both PI3K and mTOR inhibitor), CUDC-907 (inhibits both PI3K and mTOR inhibitor), AEZS-136, (also inhibits Erk1/2). AKT inhibitors include, but are not limited to, Miltefosine, VQD-002 and Perifosine.

mTOR inhibitors include, but are not limited to, ABT-578, AP-23675, AP-23573, AP-23841, CCI-779, temsirolimus, everolimus, Ridaforolimus, INK128, AZD8055, and AZD2014.

Inhibitors that inhibit both PI3K and mTOR include, but are not limited to, BEZ235, BGT226, SF1126, PKI-587.

In the MEK/ERK pathway, activated Ras activates the protein kinase activity of RAF kinase. RAF kinase phosphorylates and activates MEK (MEK1 and MEK2). MEK phosphorylates and activates a mitogen-activated protein kinase (MAPK, and originally called ERK). RAF inhibitors include, but are not limited to, SB590885, PLX4720, XL281, RAF265, LGX818, Regorafenib, RAF265, XL281, GDC0879, PLX4720, sorafenib and vemurafenib. MAPK inhibitors include, but are not limited to, XL518, CI-1040, PD035901, MEK162, selumetinib, Trametinib (GSK1120212).

Methods for making tyrosine kinase inhibitors and related compounds are well known in the art, as described above.

In another embodiment, provided herein are pharmaceutical compositions to treat a pre-cancerous skin lesions, skin tumors, and their associated diseases or disorders in a subject, comprising: a therapeutically effective amount of a tyrosine kinase inhibitor, wherein said tyrosine kinase inhibitor or related compound is present in an amount effective to treat said skin lesions, skin tumors, or their associated diseases or disorders.

The pharmaceutical compositions described herein comprise the therapeutic agents of this invention and one or more pharmaceutically acceptable carriers. "Pharmaceutically acceptable carriers" include any excipient which is nontoxic to the cell or mammal being exposed thereto at the dosages and concentrations employed. The pharmaceutical compositions may include one or more additional therapeutic agents.

According to certain embodiments, the pharmaceutical composition is a gel or ointment having the topical formulation shown in Table 1 below.

TABLE 1

| Component | Percentage (%) |
|---|---|
| Tyrosine kinase inhibitor(s) and related compounds | 0.5-1.5 |
| ethanol or DMSO | 7-9 |
| propyleneglycol | 17-19 |
| hydroxypropylmethylcellulose | 1-2 |
| Water | 70-73 |

Pharmaceutically acceptable carriers include solvents, dispersion media, buffers, coatings, antibacterial and antifungal agents, wetting agents, preservatives, buffers, chelating agents, antioxidants, isotonic agents and absorption delaying agents.

Pharmaceutically acceptable carriers include, for example, water; saline; phosphate buffered saline; dextrose; glycerol; alcohols such as ethanol and isopropanol; phosphate, citrate and other organic acids; ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; EDTA; salt forming counterions such as sodium; and/or nonionic surfactants such as TWEEN, polyethylene glycol (PEG), and PLURONICS; isotonic agents such as sugars, polyalcohols such as mannitol and sorbitol, and sodium chloride; as well as combinations thereof. Antibacterial and antifungal agents include parabens, chlorobutanol, phenol, ascorbic acid, and thimerosal.

For topical administration, embodiments of the invention may be formulated in the form of a lotion, cream, serum, spray, aerosol, cake, ointment, essence, gel, paste, patch, pencil, towelette, mask, stick, foam, elixir, concentrate, and the like form. Composition provided herein may be formulated as an immediate, controlled, extended or delayed release composition. Preparations for topical administration include aqueous or non-aqueous solutions, suspensions, emulsions, and gel. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1 M and preferably 0.05 M phosphate buffer or 0.8% saline. Other common vehicles include sodium phosphate solutions, Ringer's dextrose, dextrose and sodium chloride, lactated Ringer's, or fixed oils. Other vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

Suitable formulations for use in the therapeutic methods disclosed herein are described in Remington's Pharmaceutical Sciences, Mack Publishing Co., 16$^{th}$ ed. (1980).

In some embodiments, the composition includes isotonic agents, for example, sugars, polyalcohols, such as mannitol, sorbitol, or sodium chloride. Prolonged absorption of the compositions can be brought about by including in the composition an agent which delays absorption, for example, aluminum monostearate and gelatin.

The pharmaceutical compositions according to some embodiments of the present invention may further include a variety of pharmaceutical ingredients, which are added in order to fine-tune the consistency of the formulation, protect the formulation components from degradation and oxidation and bestow their cosmetic acceptability. Such excipients may be selected from the group consisting of water, surfactants, emulsifiers, diglycerides, triglycerides, stabilizing agents, antioxidants, glycerol, ethanol, propanol, isopropanol, butanol, polymeric gelling agents, flavoring, colorant and odorant agents and other formulation components, used in the art of pharmaceutical and cosmetic formulary.

Additional active and inactive ingredients may also include, without limitation, local analgesics such as benzocaine, menthol, and the like (wherein menthol is also capable of providing a soothing, cooling sensation), as well as, antihistamines and thickeners other than those already listed.

The compositions of the present invention can also include an emollient. Emollient is used to smooth the surface of the skin. Examples of suitable emollients include, but are not limited to, volatile and non-volatile silicone oils (e.g., dimethicone, cyclomethicone, dimethiconol, and the like), highly branched hydrocarbons, and mixtures thereof. Emollients useful in the instant invention are further described in U.S. Pat. No. 4,919,934, to Deckner et al., which is incorporated herein by reference in its entirety.

A variety of additional ingredients can be incorporated into the composition of the present invention. Non-limiting examples of these additional ingredients include vitamins and derivatives thereof (e.g., tocopherol, panthenol, and the like); other thickening agents; saturated and/or unsaturated alkyl alpha hydroxy acids; resins; gums (e.g., guar gum, xantham gum and the like); waxes (both naturally occurring and synthetic); polymers for aiding the film-forming properties and substantivity of the composition; skin bleaching (or lightening) agents including but not limited to hydroquinone, kojic acid and sodium metabisulfite; chelators and sequestrants; and aesthetic components such as fragrances, pigments, colorings, essential oils, skin sensates, astringents, skin soothing agents, skin healing agents and the like. Non-limiting examples of these aesthetic components include panthenol and derivatives (e.g., ethyl panthenol), aloe vera, pantothenic acid and its derivatives, clove oil, menthol, camphor, eucalyptus oil, eugenol, menthyl lactate, witch hazel distillate, allantoin, bisabalol, dipotassium glycyrrhizinate and the like.

The carrier system may also comprise, when desired, a suitable gelling agent including, but not limited to, cellulose esters such as hydroxypropyl cellulose, hydroxyethyl cellulose, polyvinylpyrrolidone, carboxyvinyl polymer and the like that may be provided in any amount necessary to thicken the composition to a desired gel consistency. When formulated as a gel, the base composition exhibits favorable spreadability characteristics. In addition, it remains visible on the skin surface longer, thereby instilling in the user the impression that the vehicle is more completely delivering its active ingredient(s).

In addition to the aforementioned ingredients, it should also be noted that the following ingredients may also be included in embodiments of the inventive composition, as desired: coloring agents, fragrances, conditioners, moisturizers, surfactants, antioxidants, preservatives, etc.

Effective doses of the compositions of the present invention, for treatment of conditions or diseases as described herein vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy.

The pharmaceutical compositions provided herein may include a "therapeutically effective amount." A "therapeutically effective amount" refers to an amount effective, at dosages and for periods of time necessary, to achieve the desired therapeutic result. A therapeutically effective amount of a molecule may vary according to factors such as the disease state, age, sex, and weight of the individual, and the ability of the molecule to elicit a desired response in the individual. A therapeutically effective amount is also one in which any toxic or detrimental effects of the molecule are outweighed by the therapeutically beneficial effects.

Further provided herein are kits comprising a therapeutically effective amount of a tyrosine kinase inhibitor or a related compound.

As used herein, the terms "treat" and "treatment" refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. "Treatment" can also mean prolonging survival as compared to expected survival if not receiving treatment. Those in need of treatment include those already with the disease or condition as well as those prone to having the disease or condition or those in which the disease or condition is to be prevented.

Examples of diseases which may be treated include a skin cancer associated diseases, for example, pre-cancerous skin lesions, skin tumors, and their associated diseases or disorders, or a cancer associated with the tyrosine kinase mediated signaling. Particular examples of diseases which may be treated include actinic keratosis, squamous cell carcinoma in situ like lesions, and cutaneous squamous cell carcinoma.

Methods of treating cancer may include, e.g., clearing pre-cancerous tissues, inhibiting angiogenesis in the tumor, inhibiting tumor growth, inhibiting tumor migration, inhibiting proliferation or inhibiting invasion of tumor cells.

Cancers that may be treated as described herein include those that express or overexpress or are associated with the expression or overexpression of a tyrosine kinase (e.g., SRK).

Cancers to be treated include primary tumors and secondary or metastatic tumors, as well as recurrent or refractory tumors. Recurrent tumors encompass tumors that appear to be inhibited by treatment with such agents, but recur up to five years, sometimes up to ten years or longer after treatment is discontinued. Refractory tumors are tumors that have failed to respond or are resistant to treatment with one or more conventional therapies for the particular tumor type. Refractory tumors include those that are hormone-refractory; those that are refractory to treatment with one or more chemotherapeutic agents; those that are refractory to radiation; and those that are refractory to combinations of chemotherapy and radiation, chemotherapy and hormone therapy, or hormone therapy and radiation.

Therapy may be "first-line", i.e., as an initial treatment in patients who have had no prior anti-cancer treatments, either alone or in combination with other treatments; or "second-line", as a treatment in patients who have had one prior anti-cancer treatment regimen, either alone or in combination with other treatments; or as "third-line", "fourth-line", etc. treatments, either alone or in combination with other treatments.

Therapy may also be given to patients who have had previous treatments which have been partially successful but are intolerant to the particular treatment. Therapy may also be given as an adjuvant treatment, i.e., to prevent reoccurrence of cancer in patients with no currently detectable disease or after surgical removal of tumor.

Cancers that may be treated include tumors that are not vascularized, or not yet substantially vascularized, as well as vascularized tumors. Adult tumors/cancers and pediatric tumors/cancers are included.

More than one tyrosine kinase inhibitor (e.g., SFK inhibitor) or related compound may be administered, either incorporated into the same composition or administered as separate compositions.

The tyrosine kinase inhibitor or related compound may be administered alone, or in combination with one or more therapeutically effective agents or treatments. The other therapeutically effective agent may be conjugated to the tyrosine kinase inhibitor or related compound, incorporated into the same composition as the tyrosine kinase inhibitor or related compound, or may be administered as a separate composition. The other therapeutically agent or treatment may be administered prior to, during and/or after the administration of the tyrosine kinase inhibitor or related compound.

In certain embodiments, the tyrosine kinase inhibitor or related compound is co-administered with one or more other therapeutic agents or treatments. In other embodiments, the tyrosine kinase inhibitor or related compound is administered independently from the administration of one or more other therapeutic agents or treatments. For example, the tyrosine kinase inhibitor or related compound is administered first, followed by the administration of one or more other therapeutic agents or treatments. Alternatively, one or more other therapeutic agents are administered first, followed by the administration of the tyrosine kinase inhibitor or related compound. As another example, a treatment (e.g, a surgery) is carried out first, followed by the administration of the tyrosine kinase inhibitor or related compound.

Other therapeutically effective agents/treatments include surgery, anti-neoplastics (including chemotherapeutic agents and radiation), anti-angiogenesis agents, antibodies to other targets, small molecules, photodynamic therapy, immunotherapy, cytotoxic agents, cytokines, chemokines, growth inhibitory agents, anti-hormonal agents, kinase inhibitors, cardioprotectants, immunostimulatory agents, immunosuppressive agents, and agents that promote proliferation of hematological cells.

A chemotherapeutic agent according to certain embodiments of the invention may be administered as a prodrug. The term "prodrug" refers to a precursor or derivative form of a pharmaceutically active substance that is less cytotoxic to tumor cells compared to the parent drug and is capable of being enzymatically activated or converted into the more active parent form. The prodrugs that may find use with the compositions and methods as provided herein include but are not limited to phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use with compositions and methods as provided herein include but are not limited to any of the aforementioned chemotherapeutic agents.

The administration of the tyrosine kinase inhibitor or related compound with other agents and/or treatments may occur simultaneously, or separately, via the same or different route, at the same or different times. Dosage regimens may be adjusted to provide the optimum desired response (e.g., a therapeutic or prophylactic response).

In one example, a single dose may be administered. In another example, several divided doses may be administered over time. In yet another example, a dose may be proportionally reduced or increased as indicated by the exigencies of the therapeutic situation. For multiple dosages, the composition may be, for example, administered three times a day, twice a day, once a day, once every two days, twice a week, weekly, once every two weeks, or monthly. Dosage unit form, as used herein, refers to physically discrete units suited as unitary dosages for treating mammalian subjects. Each unit may contain a predetermined quantity of active compound calculated to produce a desired therapeutic effect. In some embodiments, the dosage unit forms of the invention are dictated by and directly dependent on the unique characteristics of the active compound and the particular therapeutic or prophylactic effect to be achieved.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. An ordinarily skilled physician or veterinarian can readily determine and prescribe the effective amount of the drug required.

"Administration" to a subject is not limited to any particular delivery system and may include, without limitation, topical, transdermal, parenteral (including subcutaneous, intravenous, intramedullary, intraarticular, intramuscular, or intraperitoneal injection), rectal, or oral (for example, in capsules, suspensions or tablets). Administration may occur in a single dose or in repeat administrations, and in any of a variety of physiologically acceptable salt forms, and/or with an acceptable pharmaceutical carrier and/or additive as part of a pharmaceutical composition (described earlier). Once again, physiologically acceptable salt forms and standard pharmaceutical formulation techniques are well known to persons skilled in the art (see, e.g., Remington's Pharmaceutical Sciences, Mack Publishing Co.).

Compositions described herein (e.g., a tyrosine kinase inhibitor or related compound) may be administered topically as described herein. In some embodiments, the compositions of the present invention may be delivered to the skin using conventional dermal-type patches or articles, wherein the active ingredients of the composition is contained within a laminated structure, that serves as a drug delivery device to be affixed to the skin. In such a structure, the active ingredients of the composition are contained in a layer, or "reservoir", underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during active ingredients delivery. Examples of suitable skin contact adhesive materials include, but are not limited to, polyethylenes, polysiloxanes, polyisobutylenes, polyacrylates, polyurethanes, and the like. The particular polymeric adhesive selected will depend on the particular active ingredients, vehicle, etc., i.e., the adhesive must be compatible with all components of the active ingredients-containing composition. Alternatively, the active ingredients-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

As used herein, a "composition" refers to any composition that contains a pharmaceutically effective amount of a tyrosine kinase inhibitor or a related compound.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used herein includes both one and more than one such excipient.

The term "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In some embodiments, the subject is human.

As used herein, the term "severity" is meant to describe the potential of cancer to transform from a precancerous, or benign, state into a malignant state. Alternatively, or in addition, severity is meant to describe a cancer stage or tumor grade according to an art-recognized method.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per practice in the art. Alternatively, "about" with respect to the compositions can mean plus or minus a range of up to 20%, preferably up to 10%, more preferably up to 5%.

Any reference including patents, patent applications, or scientific publications, cited herein, are incorporated by reference in their entirety.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

EXAMPLES

Example 1

Src-family Tyrosine Kinases are Drivers of Cutaneous Neoplasia and UVB Responses in Keratinocytes, While Srcasm, a Negative Regulator of SFKs, is a Tumor Supressor Src-family tyrosine kinases (SFKs) were the first oncogenes identified, and they play central roles in promoting neoplasia in most tissues. SFKs are downstream effectors of EGFR and activate the Ras-Mek-Erk pathway in human keratinocytes. In contrast with Src, Fyn is prominently acylated on its N-terminus and localizes to lipid rafts, which are important membrane subdomains for receptor tyrosine kinase signaling. Fyn plays a major role in keratinocyte biology as lipid rafts are critical for EGFR signaling. Increased EGFR activity has been seen in a variety of human epidermal cancers including actinic keratoses, squamous cell carcinoma, and Bowen's disease.

Serial sections from 17 human AKs were analyzed for activated SFKs and

Figure 2:
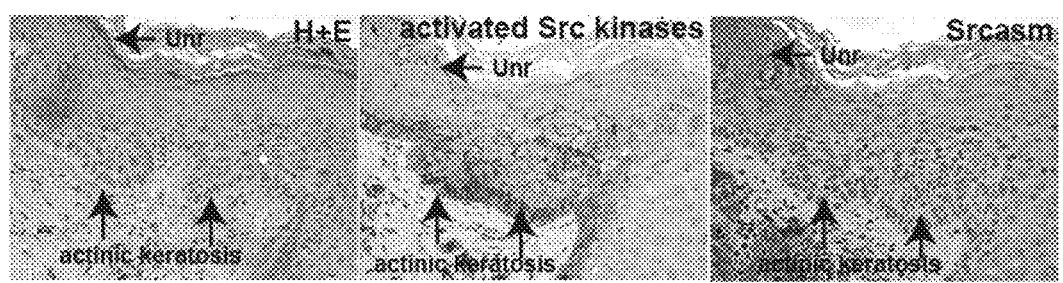
FIG. 2 demonstrates the inverse relationship between SFK activity and Srcasm levels in AKs Immunohistochemistry for activated SFKs and Srcasm shows an inverse relationship between SFK activity and Srcasm in AKs and unremarkable epidermis (Unr).

Srcasm levels Immunohistochemistry demonstrated elevated SFK activity and decreased Srcasm levels in the AKs (FIG. 2). Adjacent unremarkable epidermis (Unr) demonstrated increased SFK activity in the basal cell layer with low Srcasm levels, and decreased SFK activity with higher Srcasm levels in the suprabasilar epidermis (FIG. 2). The high prevalence of increased SFK activation in these lesions suggests that elevated SFK activity represents a key pathophysiologic feature of human AKs and sSCCs.

Figure 1:
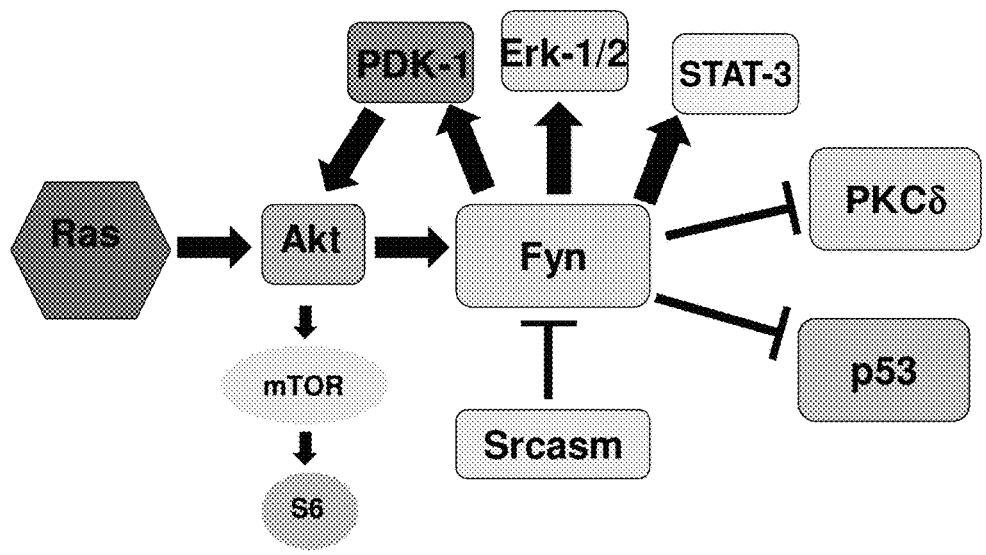
FIG. 1 Signaling model. Arrows indicate positive regulation. T-bars indicate inhibition. Fyn increases the activity of Erk 1/2, STAT-3, and PDK-1. Fyn inhibits PKCδ and p53. Srcasm negatively regulates Fyn. Ras induces Fyn mRNA levels through an Akt-dependent mechanism. PDK-1 activates Akt.

To model these observations, K14-Fyn Y528F transgenic mice were generated. These mice spontaneously develop precancerous lesions resembling human AKs and cSCCs in 5-8 weeks. Furthermore, these lesions resemble the human disease at the histologic and molecular levels. Increased Fyn activity lowers p53 levels in the precancerous lesions and cSCCs, likely through a Mek/Erk/c-Jun dependent mechanism (See FIG. 1). Recent work has shown that SFKs regulate UVB-induced protein kinase D (PKD) activity in a time- and dose-dependent manner in primary murine keratinocytes. The mechanism for activating PKD requires SFK activity. Activation of PKD in UVB-treated cells inhibits UVB-dependent apoptosis and increases the survival of keratinocytes with DNA damage, thereby promoting neoplasia. Fyn phosphorylates PKCδ, and PKCδ is an important regulator of UVB-induced apoptosis.

Srcasm (Src-activating and signaling molecule) has been shown to negatively regulate SFKs by targeting them for degradation in a lysosomal-dependent manner. Srcasm levels are decreased in human AKs and cSCCs, and Srcasm downregulation in these lesions inversely correlates with activation of SFKs in human lesions (FIG. 2). As discussed below, increasing Srcasm levels induces regression of established cSCCs in K14-Fyn Y528F mice suggesting that Srcasm levels in skin are critical for regulating cutaneous neoplasia.

Oncogenic Ras is a major driver of cSCCs. Recent in vitro data from HaCaT cells demonstrates that Fyn is a key effector of oncogenic H-Ras G12V. In these studies, oncogenic H-Ras induces Fyn mRNA >100 fold but not Src or Yes. Fyn was required for cell invasion and motility, and Fyn also was necessary for H-Ras induced activation of focal adhesion kinase (FAK). H-Ras induces Fyn mRNA levels through an Akt-dependent mechanism. Since Fyn activates the PI-3K/Akt pathway, it may amplify its own expression through a positive feedback mechanism.

Figure 3:
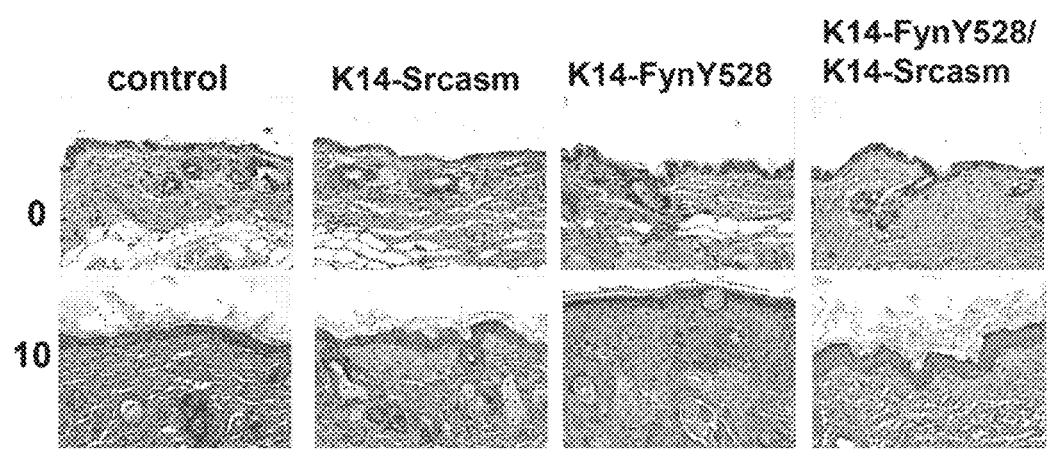
FIG. 3. K14 Fyn Y528F mice demonstrate prominent epidermal hyperplasia after acute UVB exposure. Mice (n=3) of the indicated genotypes were subjected to one dose of 1200 mJ/cm$^2$ UVB. Prominent epidermal hyperplasia was noted in K14-Fyn Y528F mice. Note that increasing Srcasm levels corrects this UV-induced hyperplasia in the K14-Fyn Y528F/K14-Srcasm double transgenic. H+E, 100×
Figure 4:
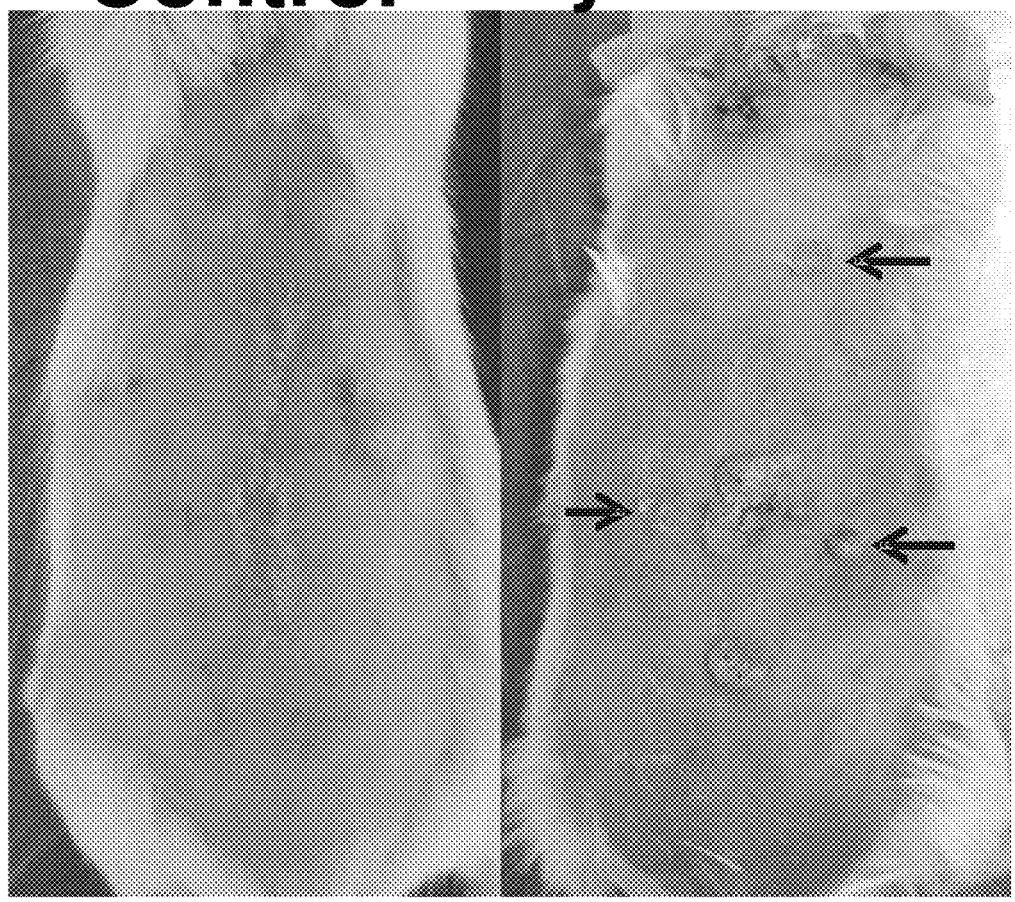
FIG. 4. K14 Fyn Y528F mice demonstrate enhanced cSCC formation after 7 weeks of UVB exposure. Six week old mice (2 per cohort) were subjected to UVB on Monday-Wednesday-Friday at 300 mJ/cm$^2$ first week, 400 mJ/cm$^2$ second week, and 500 mJ/cm$^2$ subsequent weeks. New tumor formation (avgerage 4 per mouse) was seen only in K14-Fyn Y528F mice. Arrows indicate cSCCs arising after UVB treatment. The other tumors arose before UVB.
Figure 5:
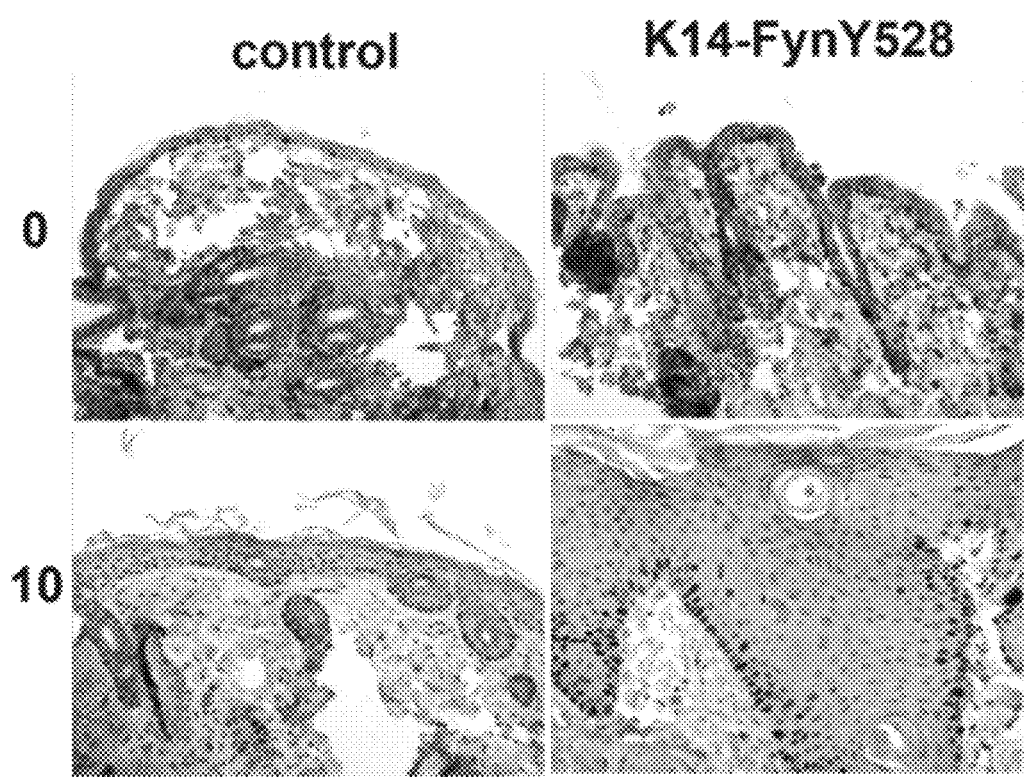
FIG. 5. Ki-67 staining demonstrates prominent UVB-induced hyperproliferation in K14-Fyn Y528F mice. Ki-67 staining of biopsies shown in FIG. 3 demonstrates increased nuclear staining of the basal and suprabasal layers in K14-Fyn Y528F mice. Sparse nuclear positivity was seen in day 0 (pre-UV) biopsies and day 10 of control mice. 200×
Figure 6:
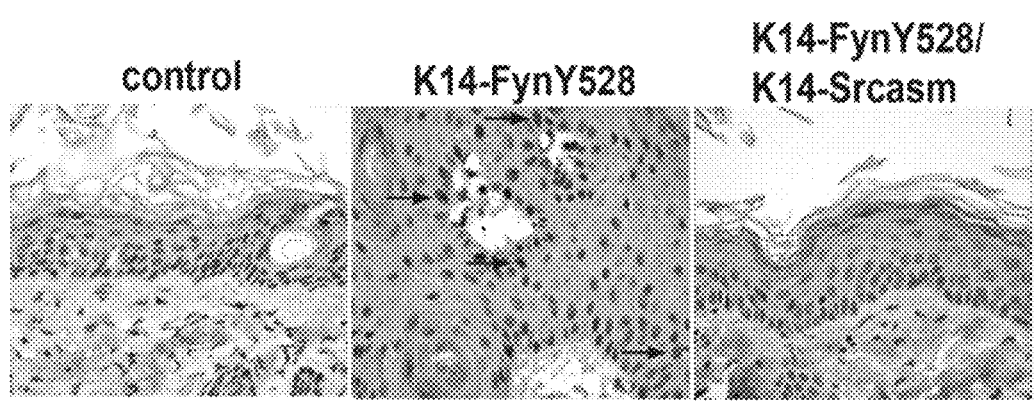
FIG. 6. K14-Fyn Y528F mice demonstrate persistent H2A.X phosphorylation. Immunohistochemical staining for phospho-H2A.X demonstrates subnuclear positivity (arrows) in K14-Fyn Y528F mice at day 10. No staining was detected in day 10 control or Fyn/Srcasm double transgenic mice. 400×

K14 Fyn Y528F mice demonstrate prominent epidermal hyperplasia and cSCCs in an UVB model. To determine if Fyn and Srcasm regulate UVB-induced responses in skin, 5-6 week old K14-Fyn Y528F, K14-Srcasm, and K14-Fyn Y528F;K14-Srcasm transgenic mice and controls were subjected to one dose of 1200 mJ/cm$^2$ of UVB. Mice were depilated two days prior to irradiation and were biopsied at distinct sites on the back at day 0 (pre-irradiation), 2, and 10; non-tumorigenic skin was biopsied in K14-Fyn Y528F mice. K14-Fyn Y528F mice demonstrated marked skin thickening by day 5; this was not seen in other cohorts (data not shown). Histologic skin sections demonstrated marked epidermal hyperplasia in K14-Fyn Y528F mice; control, K14-Srcasm, and K14-Fyn Y528F;K14-Srcasm mice all demonstrated mild epidermal hyperplasia relative to the day 0 biopsies (FIG. 3). The UVB-induced hyperplasia in K14-Fyn Y528F mice was associated with increased keratinocyte proliferation, and a persistent DNA damage response revealed by subnuclear staining for phospho-H2A.X (Ser 139)(FIGS. 5 and 6). Phospho-H2A.X nuclear staining was not seen in other day 10 or any day 0 biopsies. These data show that increased Fyn activity promotes UVB-induced epidermal hyperplasia and an activated DNA-damaged repair response. Elevated Srcasm levels in the K14-Fyn Y528F;K14-Srcasm transgenic mice corrected the UVB-induced hyperplasia and H2A.X DNA-damage response. Keratinocyte proliferation associated with DNA-damage promotes cutaneous neoplasia and suggests that K14-Fyn Y528F mice will have an increased susceptibility to UVB-induced carcinogenesis. This hypothesis was tested by chronically irradiating K14-Fyn Y528F mice and controls. K14-Fyn Y528F mice developed multiple new cSCCs after 7 weeks of UVB radiation while controls did not (FIG. 4). K14-Fyn Y528F mice do not develop new cSCCs after 11 weeks of age.

Example 2

Effect of Small Molecule Kinase Inhibitors on Precursor Lesions and Tumors in Mice As discussed in the previous example, K14-Fyn Y528F mice represent a robust model of cutaneous carcinogenesis which yields lesions that mimic human precancerous lesions; this model presents a unique in vivo screening tool to test the topical efficacy of small molecule kinase inhibitors in preventing the formation of precancerous lesions and cutaneous SCCs.

The phenotype of K14-Fyn Y528F transgenic mice yields precancerous lesions and cutaneous SCCs that resemble their human counterparts at the clinical, histologic, and molecular levels. Characterization of the K14-Fyn Y528F model demonstrates that the formation of precancerous and cSCC lesions is directly dependent on an elevated level of activated SFKs in keratinocytes.

Given the robust phenotype of the K14-Fyn Y528F mice, this transgenic line represents an excellent, physiologically relevant in vivo model for testing the efficacy of topical agents in preventing precancerous and cancerous lesions.

Topical application of the small molecule EGFR inhibitor, AG1478 (Caibiochem MW 315.8), has been shown to inhibit UV-induced tumor formation in transgenic models overexpressing v-Ras$^{Ha}$. SFK-inihibitors such as PP2 (aka AG1879, Caibiochem, MW 301.8) are slightly smaller molecules and have similar physicochemical properties as AG1478. Therefore, AG1879 may exhibit similar cutaneous absorption characteristics as AG1478, and its efficacy can be tested in inhibiting the formation of precancerous lesions and cSCCs through topical application. In addition, topical application of PP2 could be tested to determine if the compound can cause the regression of existing precancerous lesions and cSCCs. Additional supportive scientific data for testing PP2 comes from studies using radio-labeled tryphostin RG 14620, a non-specific tyrosine kinase inhibitor, (MW 275.1); this radio-labeled tyrosine kinase inhibitor applied in a white petrolatum ointment to rat skin demonstrated epidermal penetration. PP2 has a molecular weight (MW) of 301.8, and it meets the "500 dalton" rule for efficient penetration of the stratum corneum. For these reasons, it is important to test PP2 as a topical agent for treating the precancerous lesions and cSCCs in K14-Fyn Y528F mice.

Since human skin has a thicker epidermis and stratum corneum than murine skin, one may consider whether PP2 will penetrate murine skin but not human skin. However, there are studies demonstrating that the tyrosine kinase inhibitor, genistein, which bears structural semblance to PP2, can penetrate both murine skin and human skin reconstructs to inhibit UVB-induced signaling and DNA damage. Therefore, if we can show that PP2 inhibits the formation of precancerous lesions and cSCCs in K14-Fyn Y528F mice; it is likely that this compound or its congeners can be formulated to penetrate human skin efficiently.

Compounds:

5-fluorouracil (5-FU) applied as an ointment. Topical 5-FU is the first line topical agent for treating AKs in humans and can be tested as the therapeutic positive control and to validate K14-Fyn Y528F mice as a model of cutaneous neoplasia.

AG1879 (PP2, Calbiochem) applied in DMSO. AG1879 has the chemical name of 4-Amino-5-(4-chlorophenyl)-7-(t-butyl)pyrazolopyrimidine and it is a small molecule inhibitor of SFKs with a molecular weight of 301.8. AG1879 is similar structurally to AG1478, an EGFR inhibitor shown to penetrate murine skin when topically applied in DMSO. AG1879 is a potent and selective inhibitor of the Src family of protein tyrosine kinases: p59$^{fyn}$T ($IC_{50}$=5 nM) and Src ($IC_{50}$=100 nM). Since AG1879 is slightly smaller than AG1478, it is likely to penetrate the murine stratum corneum as efficiently, perhaps even more efficiently than AG1478. One can apply 10-25 µL of a 10 µm solution to a target area using the treatment regimens outlined below. The dose will be $1-2.5 \times 10^{-11}$ moles of compounds, which if completely absorbed into the circulation, would result in a maximum systemic concentration of approximately 10 nM (average weight of adult mouse 22 g-JAX labs). If phenotypic changes are seen in non-treated areas due to systemic levels of percutaneously absorbed compound, then the topical doses will be reduced in a systemic manner.

PP3 (Calbiochem) is a negative control compound for PP2 and has the chemical name 4-Amino-7-phenylpyrazolpyrimidine. PP3 will be applied in an analogous manner as PP2 in DMSO. PP3 has an $IC_{50}$=2.7 uM for EGFR which should not be an issue in treating K14-Fyn Y528F mice because Fyn is downstream of EGFR.

Phenotypic stages treated with topical agents:

SCIS-like lesion: the squamous cell carcinoma in situ (SCIS)-like lesions are manifested by hyperkeratotic plaques (FIG. 7) that appear at approximately 5-7 days post-natally and are present through 4 weeks of age. The topical agents can be applied singly to individual mice in marked treatment areas. The agent can be applied daily beginning at day 5-7, and we may initially treat for 14 days. Not all hyperkeratotic plaques will be treated to determine if systemic levels of percutaneously absorbed PP2 affect the phenotype. Initially, ten mice will be treated with each compound; ten untreated mice will serve as treatment controls. Biopsies of treated and untreated areas can be taken at day 21.

Chemoprevention of precancerous lesions and cSCCs: K14-Fyn Y528F mice develop precancerous lesions mimicking AKs and cutaneous SCCs between 5-8 weeks of age. Application of the topical agents before 5 weeks may prevent the formation of these lesions and demonstrate a chemopreventive potential for the topical agents, in this study, mice may receive topical agents to designated treatment areas beginning at 21 days and ending at day 42. Each treatment group may contain ten mice, and the non-treated control group may also comprise ten mice.

Chemoablation of pre-existing precancerous lesions and cSCCs: K14-Fyn Y528F mice develop multiple precancerous lesions and cSCCs between 5-8 weeks of age. The topical agents can be applied after the development of these lesions to determine if these compounds can function as chemoablative agents. After the development of precancerous lesions and cSCC, the topical agents can be applied to the lesions for 14-21 days. The treated and untreated lesions can be analyzed at the end of the treatment course.

Evaluation of Phenotype:

The treatment groups and control mice can be analyzed as follows.

Analysis of treated and control mice: The phenotypes of each K14-Fyn Y528F treatment group and the control group can be analyzed by counting the number of precancerous lesions and cSCCs in treated areas and non-treated areas of the treatment groups with those of control mice. Photographic documentation can be performed to monitor the phenotype. Phenotypic alterations can be analyzed by taking biopsies and subjecting the tissue to the following analytical techniques:

Microscopic analysis of skin: Skin biopsies can be taken from each treatment group in the treated and untreated areas. Parallel biopsies can be taken from the control group. One can characterize the histology of precursor lesions and cSCCs from the treatment and control cohorts. The number of precursor lesions can be determined.

Western blot analysis: Lysates from treated and control areas can be subjected to western blot analysis to detect activated SFKs, Fyn, Notch 1, NICD, Srcasm, p53, p21 and (3-actin. This can determine the mechanistic effects of topical PP2 application on skin lesions.

Statistical analysis of precancerous lesions and cSCCs: The average number of precancerous lesions and cSCCs can be determined for each treatment group and the control group. The statistical significance can be evaluated using an independent groups T-test for the means.

Interpretations: Since the K14-Fyn Y528F phenotype depends on increased Fyn activity, the topical application of PP2 can inhibit intracellular Fyn kinase activity and decrease the formation of precancerous lesions and cSCCs. Therefore, PP2 can have chemoablative effects on precursor lesions since these lesions are unlikely to acquire other genomic mutations that might promote non-Fyn dependent, autonomous growth.

Example 3

Figure 7:
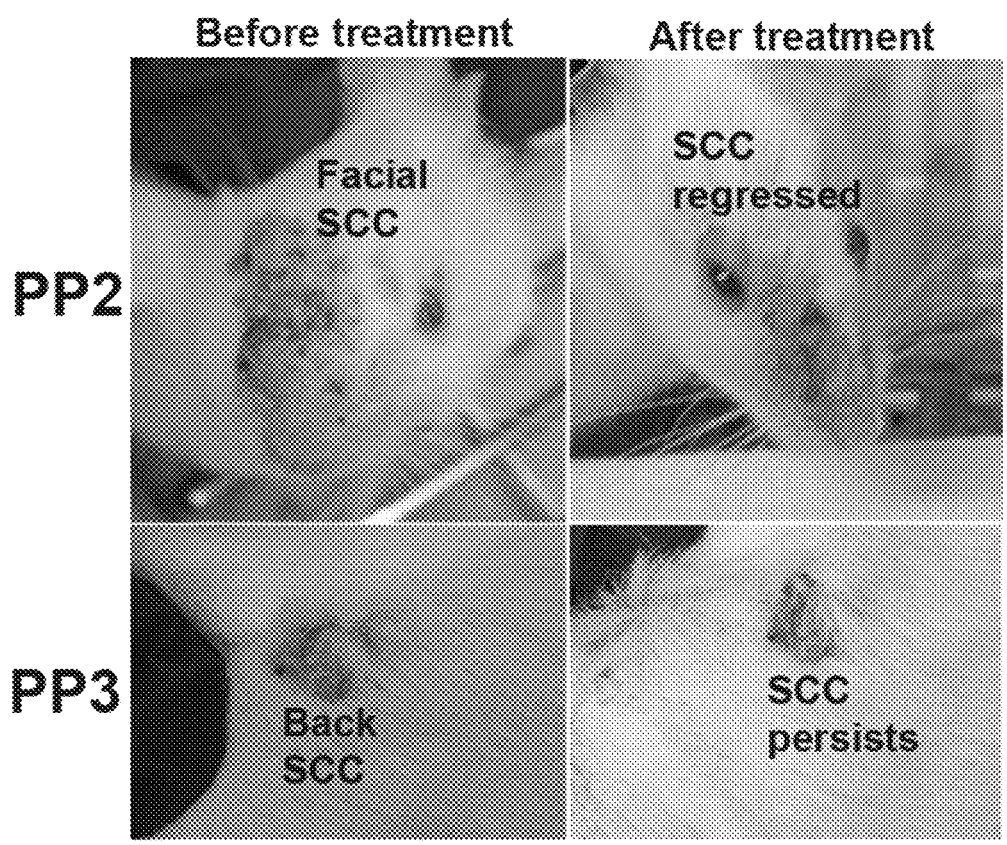
FIG. 7. Topical PP2 induces clearance of a cSCC in K14 Fyn Y528F mouse. One millimolar PP2 in DMSO (25 µL) was topically applied once a day Monday-Friday for 30 times. Clearance of a large facial cSCC was noted (top panels). A PP3 (inactive control compound) treated lesion on the same mouse remained stable (bottom panels).

Topical Application of the Small Molecule Tyrosine Kinase Inhibitor PP2 Induces Clearance of cSCCs, Clearance of Precancerous Lesion, and Tumor Regression in Mice To determine the effects of topical application of tyrosine kinase inhibitors, PP2 was applied topically to a cohort of five K14-Fyn Y528F mice with a total of 11 cSCCs. PP2 is a well characterized inhibitor of Src-family tyrosine kinases with a molecular weight of 301.8 daltons; therefore, this compound is smaller than 500 daltons, which is the molecular weight cut-off for penetrating the skin efficiently. Tumors received approximately 25 µL of 1 mM (a 0.03% solution) PP2 daily for 30 days (Monday thru Friday) and were evaluated by photography before initiating treatment and every Friday for 6 weeks. As a control, a cohort of 4 mice with 9 cSCCs was treated analogously with PP3, an inactive PP2 analog. The cSCCs represent keratotic tumors larger than 3×3 mm (as measured by calipers). All PP2 treated tumors (N=11) demonstrated significant tumor regression as defined by a 75% or greater decrease in tumor area. None (N=9) of the PP3 treated tumors demonstrated 75% regression during the treatment period. These results are statistically significant with p<0.01. One mouse received PP2 to a large facial cSCC and PP3 to a back cSCC; the facial tumor regressed by the end of the 6 weeks while the back cSCC was unchanged (FIG. 7). These data demonstrate that PP2 and related compounds are useful for topically treating cSCCs in the K14-Fyn Y528F mice. The data show that these small molecule kinase inhibitors can be more potent than existing agents which are used as 0.5% to 5% formulations. It appears that systemic absorption of the PP2 under these conditions did not affect the growth of non-treated tumors on the same mouse.

Figure 8:
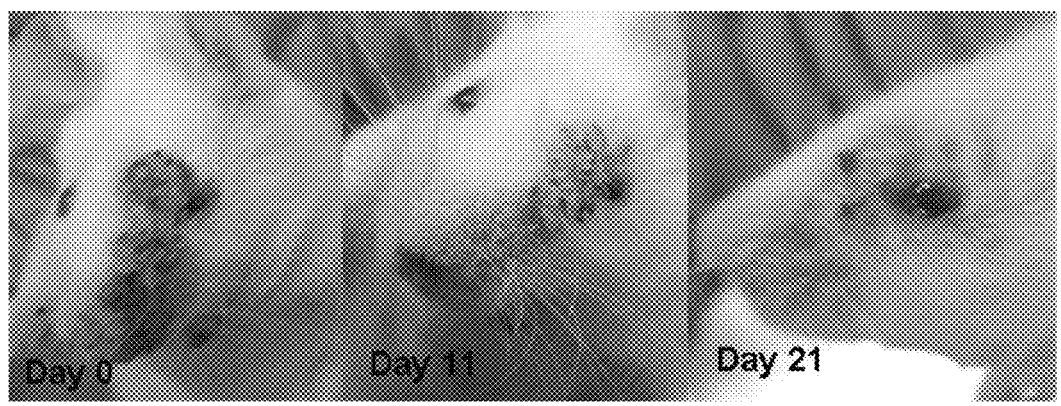
FIG. 8. Topical PP2 induces clearance of cSCC in K14 Fyn Y528F mice as early as 21 days. One millimolar PP2 in DMSO was topically applied once a day Monday-Saturday for 20 times. Clearance of a large facial cSCC was noted by 21 days.

FIG. 8 shows that topical PP2 can induce clearance of cSCC in K14-Fyn Y528F mice as early as 21 days. One millimolar PP2 in DMSO was topically applied once a day Monday-Saturday for 20 times. Clearance of a large facial cSCC was noted by 21 days.

Figure 9:
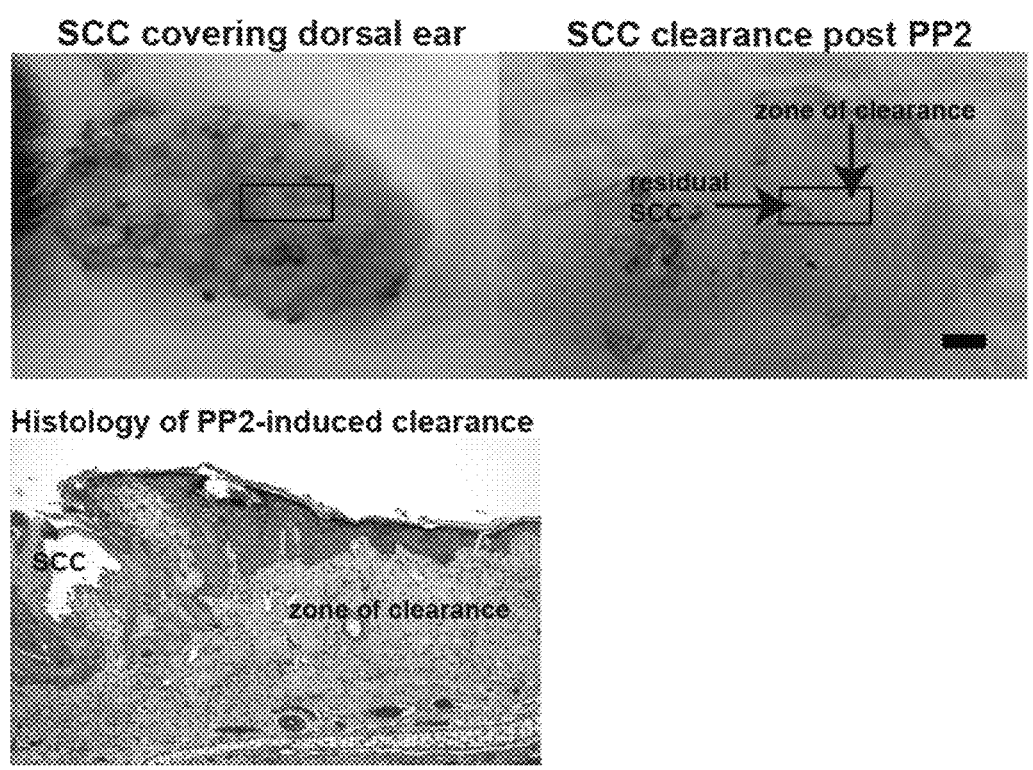
FIG. 9. Histologic features of PP2-induced clearance of cSCC in K14 Fyn Y528F mice. One millimolar PP2 in DMSO was topically applied once a day Monday-Friday for 30 times to a cSCC covering the dorsum of the ear. Prominent clearance of the cSCC was noted six weeks after beginning treatment. The open rectangle designates the region of the ear taken for histology. Small black rectangle=1 mm FIG. 10. Clearance of precancerous lesion and a cSCC by PP2 in three weeks. One millimolar PP2 in DMSO was topically applied once a day Monday-Friday for 20 times to a small precancerous lesion on the ear and to a cSCC on the neck. Clearance of both lesions was noted by three weeks after initiating treatment. Small black rectangle=2 mm

To better understand the effect of topical PP2 treatment, a histologic analysis of tissue demonstrating tumor clearance was performed. An ear covered with a cSCC as manifested by nodular masses, hyperkeratosis, and crusting, was treated 30 times with 1 mM PP2 in DMSO (FIG. 9). Histologic features of PP2-induced clearance of cSCC in K14-Fyn Y528F mice. One millimolar PP2 in DMSO was topically applied once a day Monday-Friday for 30 times to a cSCC covering the dorsum of the ear. Prominent clearance of the cSCC was noted six weeks after beginning treatment.

Prominent clearance of the tumor was noted with smoothening of the skin surface and re-growth of hair. The histologic sections of this area show a small focus of residual cSCC adjacent to a zone of epidermal hyperplasia and mild mixed dermal inflammation. Notably absent are prominent inflammation, ulceration, or skin peeling, as might be seen with 5-FU treatment.

Figure 10:
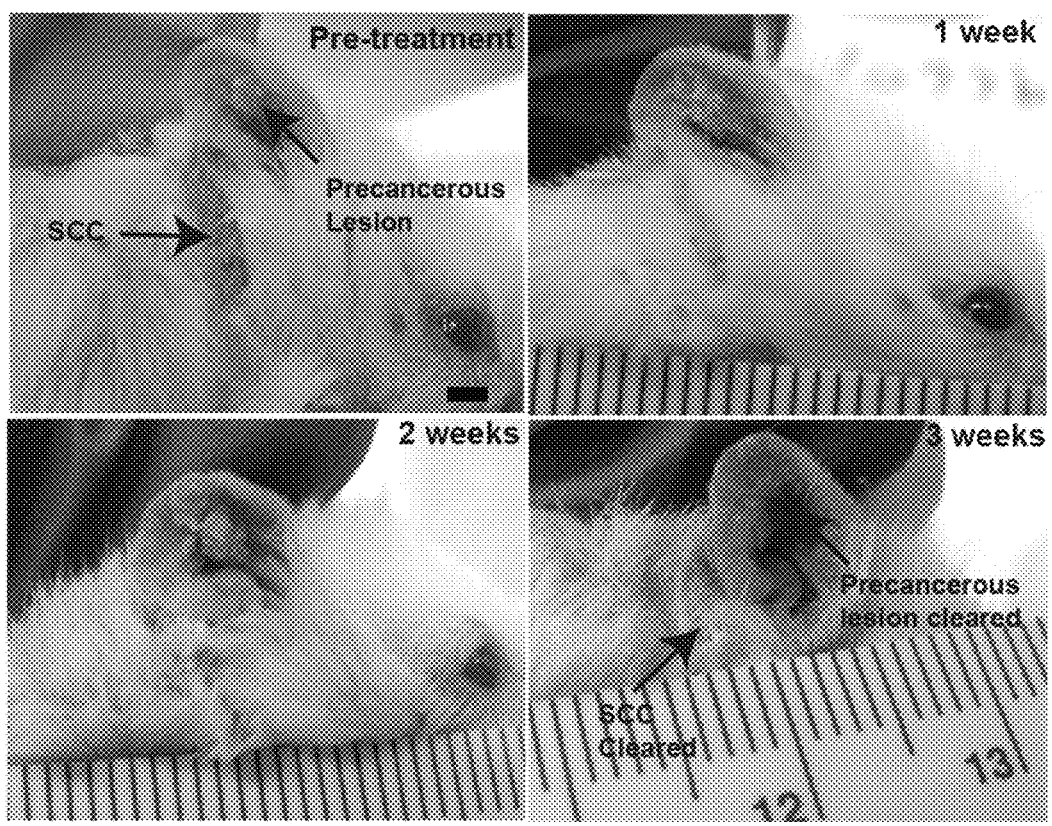
Figure 11:
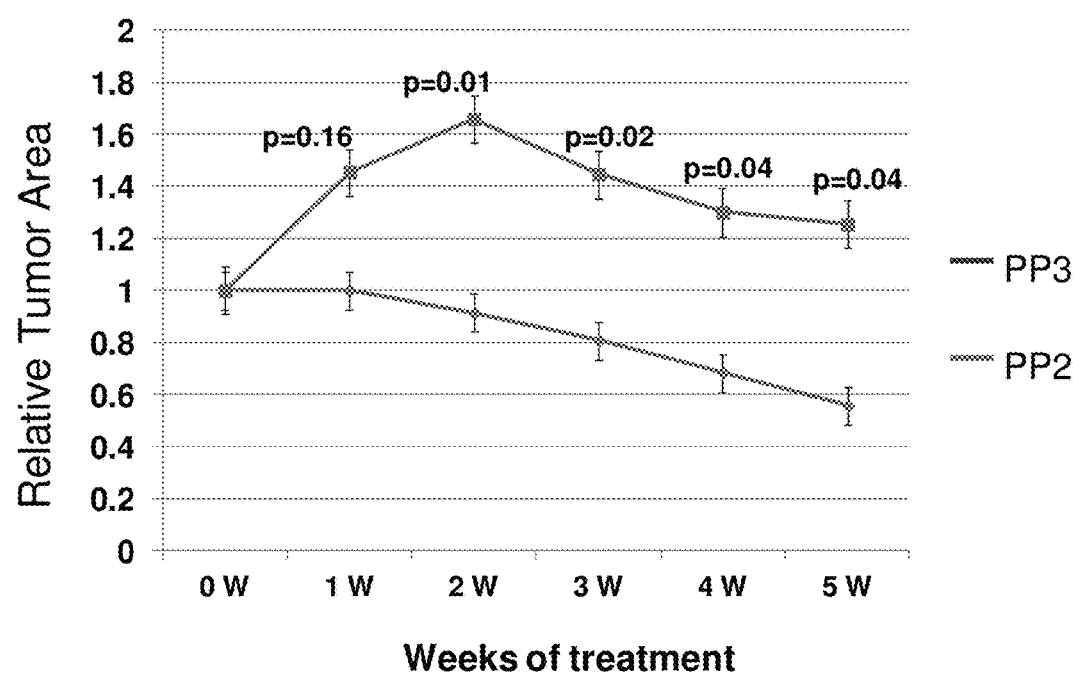
FIG. 11 shows that topical PP2 induces tumor regression in five weeks.
Figure 12:
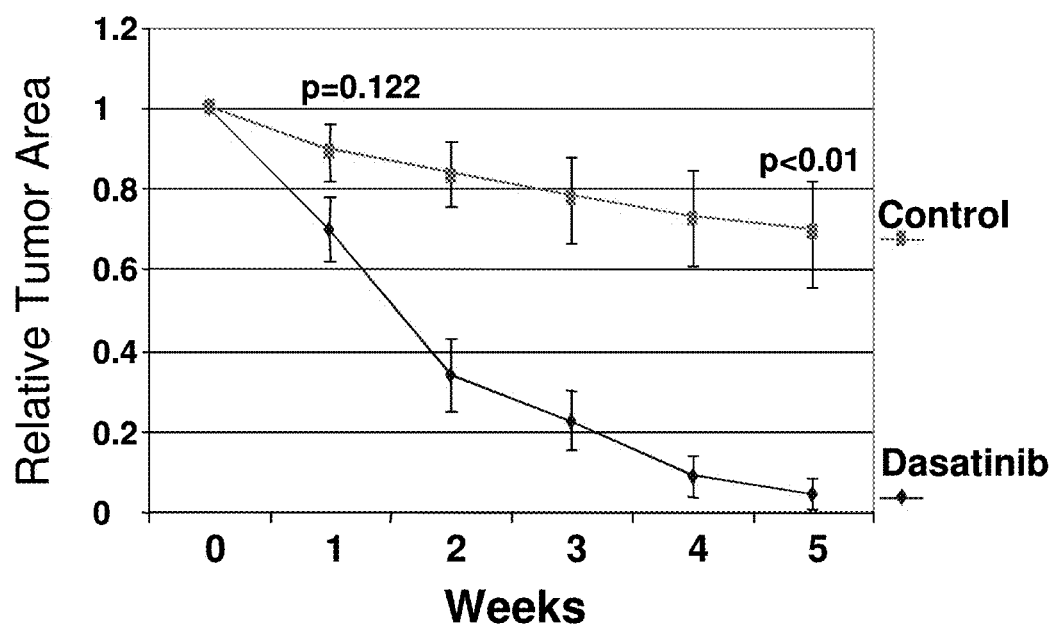
FIG. 12 shows that topical dasatinib reduces cSCC size in cohort study. 11 K14-Fyn Y528F mice with solitary cSCCs were given topical 1% dasatinib ointment daily (Monday-Friday) for 25 applications. A control cohort of 6 mice was treated in parallel with vehicle.

As shown in FIG. 10, PP2 induces clearance of precancerous lesion in three weeks. One millimolar PP2 in DMSO was topically applied once a day Monday-Friday for 20 times to a small precancerous lesion on the ear and to a cSCC on the neck. Clearance of both lesions was noted by three weeks after initiating treatment. FIG. 11 shows that PP2 induces tumor regression in five weeks.

Example 4

Topical Application of Dasatinib Induces cSCC Regression

Dasatanib (BMS-354825) (N-(2-chloro-6-methylphenyl)-2-[[6-[4-(2-hydroxyethyl)-1-piperazinyl]-2-methyl-4-pyrimidinyl]amino]-5-thiazolecarboxamide, monohydrate) is a small molecule protein kinase inhibitor where the free base has a Molecular Weight of 488.01 daltons, and which is FDA approved for systemic use in the treatment of certain hematological cancers. As a small molecule kinase inhibitor (SMKIs) (i.e., <500 daltons), dasatanib is likely to penetrate both mouse and human skin. Furthermore, as an SMKI that is FDA approved for systemic use, its toxicology profile would make its approval for topical use less burdensome. Thus the efficacy of topical dasatinib, a tyrosine kinase inhibitor, was tested on cSCCs in K14-Fyn Y528F mice. Topical 1% dasatinib ointment, formulated as shown in Table 2 below, was applied daily (Monday-Friday) to a cohort of 11 mice with solitary cSCCs. A control cohort of six mice with solitary cSCCs was treated with ointment only. Topical dasatinib induced a marked regression of cSCCs in the treatment group with only 4% of the original tumor area remaining after 5 weeks (FIGS. 10 and 11).

TABLE 2

Dasatanib Formulation

| Component | Percentage (%) |
|---|---|
| Dasatinib | 1 |
| DMSO | 8 |
| Propyleneglycol | 18 |
| hydroxypropylmethylcellulose | 1 |
| Water | 72 |

Example 5

Topical Application of BEZ235 Induces cSCC Regression

BEZ235 (2-Methyl-2-{4-[3-methyl-2-oxo-8-(quinolin-3-yl)-2,3-dihydro-1H-imidazo[4,5-c[quinolin-1-yl [phenyl}propanenitrile) is an inhibitor of PI-3 and mTOR kinases, and these kinases are activated in K14-Fyn Y528F cSCCs.

Phosphorylation of S6 kinase, an mTOR substrate, is elevated in these cSCCs (FIG. 15, right panel) (right panel) as compared to unremarkable tissue (FIG. 15, left panel). Briefly, immunohistochemistry (IIIC) on formalin fixed paraffin embedded (FFPE) tissue sections, 5 µm thick, was performed using a rabbit specific DAB detection System Kit (Spring Bioscience, Pleasanton, CA). Slides were deparaffinized in two xylenes and were rehydrated through a series of downgraded alcohols (100, 95, 70, and 50). Heat-mediated antigen retrieval was performed using 10 mM Citrate Buffer, pH 6.0. To quench the endogenous peroxidase, the slides were immersed in freshly prepared 2% $H_2O_2$, and incubated in the dark for 15 minutes. Slides were then washed and incubated for one hour in blocking buffer (10% normal goat serum, 1% BSA). The blocking buffer was removed and the tissue sections were incubated overnight at 4° C. with a 1:70 dilution of a rabbit anti-S6 andibody (Cell Signaling, Danvers, Mass.). The next day the tissue sections were washed in TBS. Followed by incubation with HRP conjugated secondary antibodies for 40 minutes, signal was amplified with the DAB solution.

The efficacy of a 20 mM topical BEZ235 ointment, formulated as in the previous example, was evaluated in inducing regression of cSCCs in K14-Fyn Y528F mice. Topical BEZ235 ointment was applied daily (Monday-Friday) to a cohort of 15 mice with solitary cSCCs. A control cohort of 15 mice with solitary cSCCs was treated with ointment alone. The size range of tumors was similar in each cohort. Topical BEZ235 induced a marked regression of cSCCs in the treatment group compared to controls (FIG. 14). In the BEZ235 cohort, 80% of tumors completely regressed by five weeks, including many larger lesions >25 $mm^2$; in controls, tumor shrinkage was seen in small lesions <15 $mm^2$ and this cohort has more small lesions. This data show that targeting kinases activated downstream of Fyn induces cSCC regression.

Example 6

Topical Application of U0126 Induces cSCC Regression

U0126 (1,4-diamino-2,3-dicyano-1,4-bis(2-aminophenylthio)butadiene) is a selective inhibitor of both MEK1 and MEK2, both MAPK/ERK kinase family members, and these kinases are activated in K14-Fyn Y528F cSCCs. The efficacy of a 1% topical U0126 ethanol or DMSO gel or ointment, formulated as in the previous examples, was evaluated for inducing regression of cSCCs in K14-Fyn Y528F mice. Topical U0126 ointment was applied daily (Monday-Friday) to a cohort of 8 mice with 11 cSCCs. Topical U0126 ointment was applied to each cSCC daily (Monday-Friday) for three weeks. The final measurement of cSCC sizes were conducted one week following the end of treatment.

TABLE 3

Treatment of cSCCs with U0126

| Initial cSCC size (mm$^2$) | Final cSCC size (mm$^2$) |
|---|---|
| 4 | cSCC resolved |
| Excluded lesion too small | |
| 9 | 1 |
| 9 | 1 |
| 14 | cSCC unchanged |
| 8 | 6 |
| 12 | cSCC resolved |
| 50 | 1 |
| Excluded No Final Measurement Performed | |
| 12 | cSCC resolved |
| 1 | 8 |

As a control, 2 mice with 2 cSCCs were treated analogously with U0124 (2,3-Bis-[1-amino-1-methylsulfanylmeth-(Z)-ylidene]-succinonitrile), an inactive U0126 analog. Two of the cSCCs treated with U0124 stayed the same size at 1 $mm^2$ Topical U0126 induces a marked regression of cSCCs in the treatment group compared to controls of 75 +/-37% compared to 0% for U0124.

Example 7

Topical Application of Selumetinib Induces cSCC Regression

Selumetinib (AZD6244) (6-(4-bromo-2-chlorophenylamino)-7-fluoro-N-(2-hydroxyethoxy)-3-methyl-3H-benzo[d]imidazole-5-carboxamide) is an MEK1 inhibitor. The efficacy of a 1% topical Selumetinib ethanol or DMSO gel or ointment, formulated as in the previous examples, is evaluated for inducing regression of cSCCs in K14-Fyn Y528F mice. Topical Selumetinib ointment is applied daily (Monday-Friday) to a cohort of 15 mice with solitary cSCCs. A control cohort of 15 mice with solitary cSCCs is treated with ointment alone. The size range of tumors is similar in each cohort. Topical Selumetinib induces a marked regression of cSCCs in the treatment group compared to controls.

Example 8

Topical Application of Tofacitinib Induces cSCC Regression

Tofacitinib (CP-690,550) (3-[(3R,4R)-4-methyl-3-[methyl(7H-pyrrolo[2,3 -d]pyrimidin-4-yl)amino]piperidin-1-yl]-3-oxopropanenitrile) is a Janus kinase (JAK) inhibitor. Tofacitinib citrate is FDA approved for oral administration in the treatment of rheumatoid arthritis. The free base has a Molecular Weight of 312.4 daltons. The efficacy of a 1% topical Tofacitinib ethanol or DMSO gel or ointment, formulated as in the previous examples, is evaluated for inducing regression of cSCCs in K14-Fyn Y528F mice. Topical Tofacitinib ointment is applied daily (Monday-Friday) to a cohort of 15 mice with solitary cSCCs. A control cohort of 15 mice with solitary cSCCs is treated with ointment alone. The size range of tumors is similar in each cohort. Topical Tofacitinib induces a marked regression of cSCCs in the treatment group compared to controls.

Example 9

Topical Application of Saracatinib Induces cSCC Regression

Saracatinib (N-(5-chlorobenzo[d][1,3 ]dioxol-4-yl)-7-(2-(4-methylpiperazin-1-yl)ethoxy)-5-(tetrahydro-2H-pyran-4-yloxy)quinazolin-4-amine) potently inhibits Src tyrosine kinase family members including Fyn. The efficacy of a 1% topical Saracatinib ethanol or DMSO gel or ointment, formulated as in the previous examples, is evaluated for inducing regression of cSCCs in K14-Fyn Y528F mice. Topical Saracatinib ointment is applied daily (Monday-Friday) to a cohort of 15 mice with solitary cSCCs. A control cohort of 15 mice with solitary cSCCs is treated with ointment alone. The size range of tumors is similar in each cohort. Topical Saracatinib induces a marked regression of cSCCs in the treatment group compared to controls.

Example 10

Topical Application of CEP-11981 Induces cSCC Regression

CEP-11981 (13-isobutyl-4-methyl-10-(pyrimidin-2-ylamino)-4,7,8,13-tetrahydro-1H-indazolo[5,4-a]pyrrolo[3,4-c]carbazol-6(2H)-one) is a tyrosine kinase inhibitor, including Src tyrosine kinase family members. The efficacy of a 1% topical CEP-11981 ethanol or DMSO gel or ointment, formulated as in the previous examples, is evaluated for inducing regression of cSCCs in K14-Fyn Y528F mice. Topical CEP-11981 ointment is applied daily (Monday-Friday) to a cohort of 15 mice with solitary cSCCs. A control cohort of 15 mice with solitary cSCCs is treated with ointment alone. The size range of tumors is similar in each cohort. Topical CEP-11981 induces a marked regression of cSCCs in the treatment group compared to controls.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method for treating a skin cancer related disease or disorder in a subject, the method comprising: topically administering to said subject a therapeutically effective amount of a PI3K/PDK1/AKT signaling pathway kinase inhibitor, wherein the disease or disorder is actinic keratosis, a squamous cell carcinoma in situ like lesion, or a cutaneous squamous cell carcinoma.

2. The method of claim 1, wherein said disease or disorder is actinic keratosis.

3. The method of claim 1, wherein said disease or disorder is a squamous cell carcinoma in situ like lesion.

4. The method of claim 1, wherein said disease or disorder is associated with cutaneous squamous cell carcinoma.

5. The method of claim 1, wherein said inhibitor is administered in combination with at least one other treatment regime selected from the group consisting of chemotherapy, immunotherapy, radiation therapy, photodynamic therapy, electrocautery, laser therapy, and surgery.

6. The method of claim 1, wherein said subject is a human.

7. The method of claim 1, wherein said inhibitor has a molecular weight of less than 500 daltons.

8. A method for treating a skin cancer related disease or disorder in a subject, the method comprising: topically administering to said subject a therapeutically effective amount of a MAPK/ERK signaling pathway kinase inhibitor, wherein the disease or disorder is actinic keratosis, a squamous cell carcinoma in situ like lesion, or a cutaneous squamous cell carcinoma.

9. The method of claim 8, wherein said disease or disorder is actinic keratosis.

10. The method of claim 8, wherein said disease or disorder is a squamous cell carcinoma in situ like lesion.

11. The method of claim 8, wherein said disease or disorder is associated with cutaneous squamous cell carcinoma.

12. The method of claim 8, wherein said inhibitor is administered in combination with at least one other treatment regime selected from the group consisting of chemotherapy, immunotherapy, radiation therapy, photodynamic therapy, electrocautery, laser therapy, and surgery.

13. The method of claim 8, wherein said subject is a human.

14. The method of claim 8, wherein said inhibitor has a molecular weight of less than 500 daltons.

15. A method for treating a skin cancer related disease or disorder in a subject, the method comprising: topically administering to said subject a therapeutically effective amount of a JAK-STAT signaling pathway kinase inhibitor, wherein the disease or disorder is actinic keratosis, a squamous cell carcinoma in situ like lesion, or a cutaneous squamous cell carcinoma.

16. The method of claim 15, wherein said disease or disorder is actinic keratosis.

17. The method of claim 15, wherein said disease or disorder is a squamous cell carcinoma in situ like lesion.

18. The method of claim 15, wherein said disease or disorder is associated with cutaneous squamous cell carcinoma.

19. The method of claim 15, wherein said inhibitor is administered in combination with at least one other treatment regime selected from the group consisting of chemotherapy, immunotherapy, radiation therapy, photodynamic therapy, electrocautery, laser therapy, and surgery.

20. The method of claim 15, wherein said subject is a human.

21. The method of claim 15, wherein said inhibitor has a molecular weight of less than 500 daltons.

22. A method for treating a skin cancer related disease or disorder in a subject, the method comprising: topically administering to said subject a therapeutically effective amount of a compound, wherein the compound comprises a kinase inhibitor that inhibits both PI3K and mTOR and wherein the disease or disorder is actinic keratosis, a squamous cell carcinoma in situ like lesion, or a cutaneous squamous cell carcinoma.

23. A method for treating a skin cancer related disease or disorder in a subject, the method comprising topically administering to said subject a therapeutically effective amount of CEP-11981 and a pharmaceutically acceptable carrier, wherein the skin cancer related disease is selected from the group consisting of actinic keratosis, a squamous cell carcinoma in situ like lesion, and a cutaneous squamous cell carcinoma.

24. The method of claim 1, wherein the PI3K/PDK1/AKT signaling pathway kinase inhibitor comprises a lipid kinase inhibitor.

25. The method of claim 1, wherein the PI3K/PDK1/AKT signaling pathway kinase inhibitor comprises a protein kinase inhibitor.

26. The method of claim 25, wherein the protein kinase inhibitor comprises a serine-threonine kinase inhibitor.

27. The method of claim 25, wherein the protein kinase inhibitor comprises a serine-threonine kinase inhibitor and a tyrosine kinase inhibitor.

28. The method of claim 1, wherein the PI3K/PDK1/AKT signaling pathway kinase inhibitor is a PI3K inhibitor.

29. The method of claim 1, wherein the PI3K/PDK1/AKT signaling pathway kinase inhibitor is an AKT inhibitor.

30. The method of claim 1, wherein the PI3K/PDK1/AKT signaling pathway kinase inhibitor is an mTOR inhibitor.

31. The method of claim 8, wherein the MAPK/ERK signaling pathway kinase inhibitor comprises a lipid kinase inhibitor.

32. The method of claim 8, wherein the MAPK/ERK signaling pathway kinase inhibitor comprises a protein kinase inhibitor.

33. The method of claim 32, wherein the protein kinase inhibitor comprises a serine-threonine kinase inhibitor.

34. The method of claim 32, wherein the protein kinase inhibitor comprises a serine-threonine kinase inhibitor and a tyrosine kinase inhibitor.

35. The method of claim 8, wherein the MAPK/ERK signaling pathway kinase inhibitor is a RAF inhibitor.

36. The method of claim 8, wherein the MAPK/ERK signaling pathway kinase inhibitor is a MAPK inhibitor.

37. The method of claim 15, wherein the JAK-STAT signaling pathway kinase inhibitor comprises a lipid kinase inhibitor.

38. The method of claim 15, wherein the JAK-STAT signaling pathway kinase inhibitor comprises a protein kinase inhibitor.

39. The method of claim 38, wherein the protein kinase inhibitor comprises a serine-threonine kinase inhibitor.

40. The method of claim 38, wherein the protein kinase inhibitor comprises a serine-threonine kinase inhibitor and a tyrosine kinase inhibitor.

41. The method of claim 15, wherein the JAK-STAT signaling pathway kinase inhibitor is a JAK or STAT inhibitor.

42. The method of claim 15, wherein the kinase inhibitor that inhibits both PI3K and mTOR comprises a lipid kinase inhibitor.

43. The method of claim 15, wherein the kinase inhibitor that inhibits both PI3K and mTOR comprises a protein kinase inhibitor.

44. The method of claim 43, wherein the protein kinase inhibitor comprises a serine-threonine kinase inhibitor.

45. The method of claim 43, wherein the protein kinase inhibitor comprises a serine-threonine kinase inhibitor and a tyrosine kinase inhibitor.

46. The method of claim 23, wherein the disease or disorder is actinic keratosis, a squamous cell carcinoma in situ like lesion, or a cutaneous squamous cell carcinoma.

* * * * *

UNITED STATES PATENT AND TRADEMARK OFFICE
CERTIFICATE OF CORRECTION

| | | |
|---|---|---|
| PATENT NO. | : 9,555,034 B2 | Page 1 of 1 |
| APPLICATION NO. | : 14/803352 | |
| DATED | : January 31, 2017 | |
| INVENTOR(S) | : John T. Seykora | |

It is certified that error appears in the above-identified patent and that said Letters Patent is hereby corrected as shown below:

In the Specification

In Column 1, Line 15, please insert the following:
--GOVERNMENT INTEREST STATEMENT
This invention was made with government support under grant numbers AR051380 and CA165836 awarded by the National Institutes of Health. The government has certain rights in the invention.--

Signed and Sealed this
Nineteenth Day of February, 2019

Andrei Iancu
*Director of the United States Patent and Trademark Office*